(12) United States Patent
Gelbman

(10) Patent No.: US 9,714,954 B2
(45) Date of Patent: Jul. 25, 2017

(54) MULTIPLE CARRIER AND SLEEVE TRAY

(71) Applicant: Alexander Gelbman, Lake Worth, FL (US)

(72) Inventor: Alexander Gelbman, Lake Worth, FL (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 42 days.

(21) Appl. No.: 14/439,616

(22) PCT Filed: Nov. 1, 2013

(86) PCT No.: PCT/US2013/068112
§ 371 (c)(1),
(2) Date: Apr. 29, 2015

(87) PCT Pub. No.: WO2014/071214
PCT Pub. Date: May 8, 2014

(65) Prior Publication Data
US 2015/0301072 A1    Oct. 22, 2015

Related U.S. Application Data

(60) Provisional application No. 61/721,411, filed on Nov. 1, 2012.

(51) Int. Cl.
*G01N 35/04* (2006.01)
*G01N 35/02* (2006.01)
*G01N 35/00* (2006.01)

(52) U.S. Cl.
CPC ........... *G01N 35/021* (2013.01); *G01N 35/02* (2013.01); *G01N 35/04* (2013.01);
(Continued)

(58) Field of Classification Search
CPC ........... G01N 35/02; G01N 2035/0429; G01N 2035/0465; G01N 2035/0401; G01N 2035/0444
See application file for complete search history.

(56) References Cited

U.S. PATENT DOCUMENTS 4,748,993 A * 6/1988 Llewellyn ............. A47L 15/505
134/135
5,080,232 A * 1/1992 Leoncavallo ............. B01L 9/06
206/443

(Continued)

FOREIGN PATENT DOCUMENTS

WO    2013/116638 A1    8/2013

OTHER PUBLICATIONS

PCT International Search Report and Written Opinion dated Apr. 8, 2014 (9 Pages).

*Primary Examiner* — Paul Hyun

(57) ABSTRACT

An automation system for use with in-vitro diagnostics that includes a track configured to provide one or more paths and a plurality of sleeves. Each sleeve is configured to hold one of a plurality of fluid containers. The system also includes a plurality of carriers configured to travel along the track. Each carrier is separable from each sleeve and configured to hold one of the plurality of sleeves. The system further includes a tray having a plurality of rows. Each row is configured to hold at least one of: (i) one or more of the plurality of sleeves; and (ii) one or more of the plurality of carriers. The tray is configured to at least one of: (i) unload the plurality of sleeves or the plurality of carriers from the tray; and (ii) load the plurality of sleeves or the plurality of carriers to the tray.

10 Claims, 23 Drawing Sheets

(52) U.S. Cl.
CPC ............. *G01N 2035/00782* (2013.01); *G01N 2035/00801* (2013.01); *G01N 2035/00891* (2013.01); *G01N 2035/0429* (2013.01); *G01N 2035/0465* (2013.01)

(56) References Cited

U.S. PATENT DOCUMENTS

| | | | |
|---|---|---|---|
| 7,648,321 | B2 | 1/2010 | Neeper et al. |
| 2004/0136869 | A1* | 7/2004 | Itoh ........................ G01N 35/04 422/65 |
| 2005/0196323 | A1* | 9/2005 | Itoh .................. G01N 35/00732 422/82.05 |
| 2005/0265901 | A1* | 12/2005 | Sinclair ..................... B01L 9/06 422/552 |
| 2009/0003981 | A1 | 1/2009 | Miller |
| 2010/0129789 | A1 | 5/2010 | Self et al. |
| 2010/0294046 | A1 | 11/2010 | Boeke et al. |
| 2012/0283867 | A1 | 11/2012 | Gelbman et al. |

\* cited by examiner

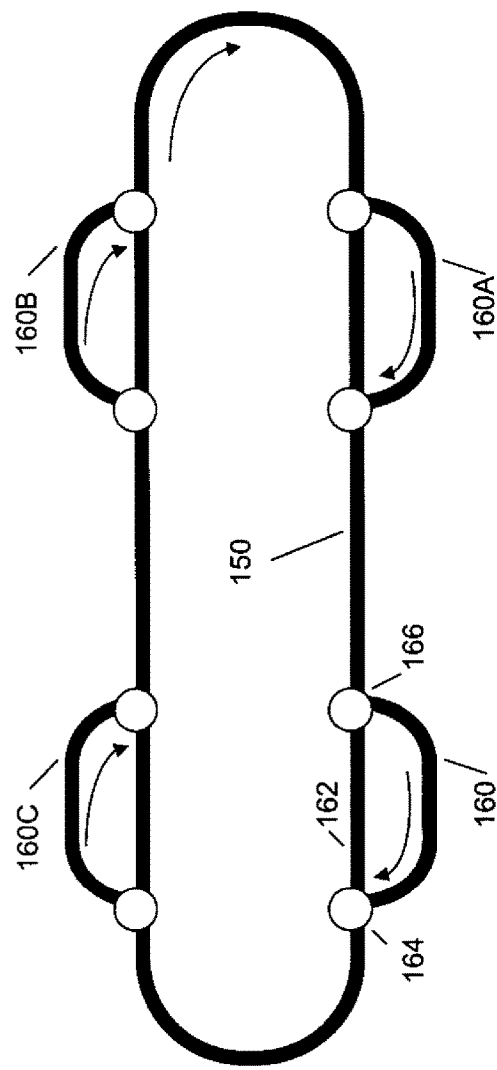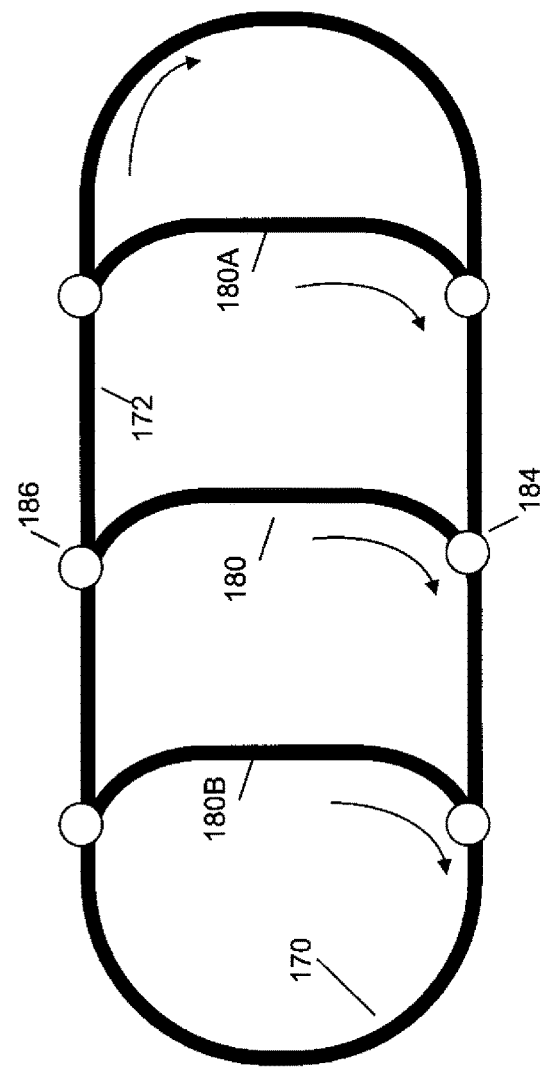

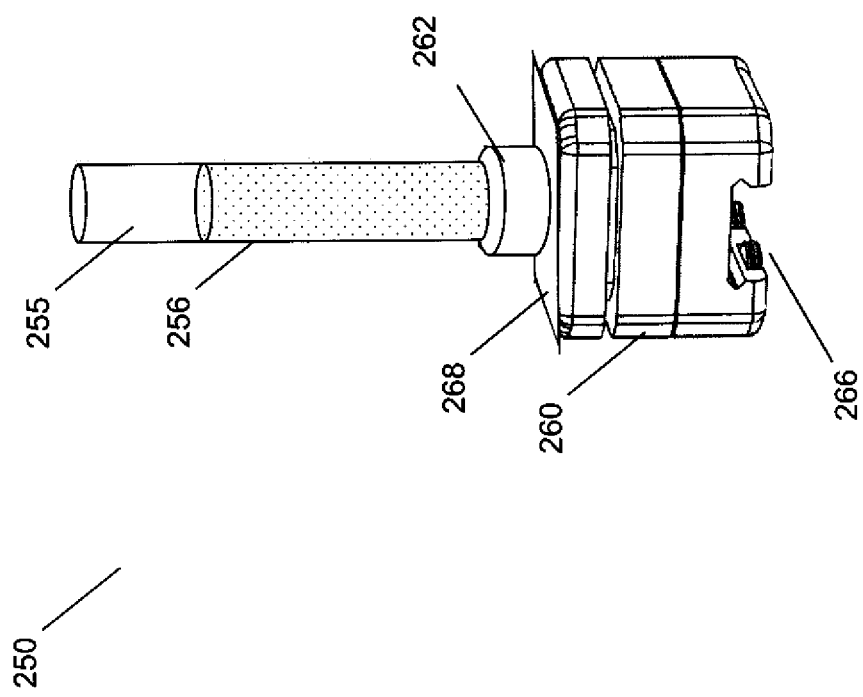

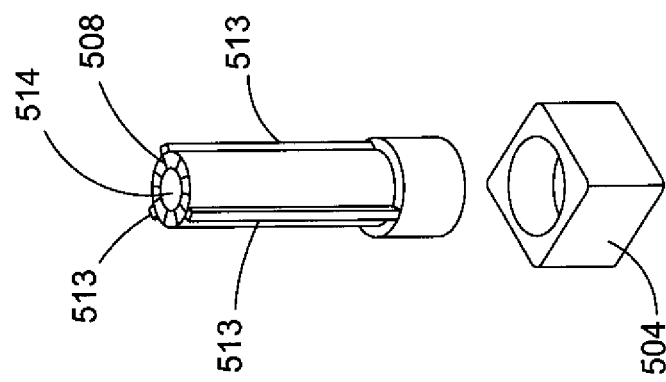
FIG. 5C
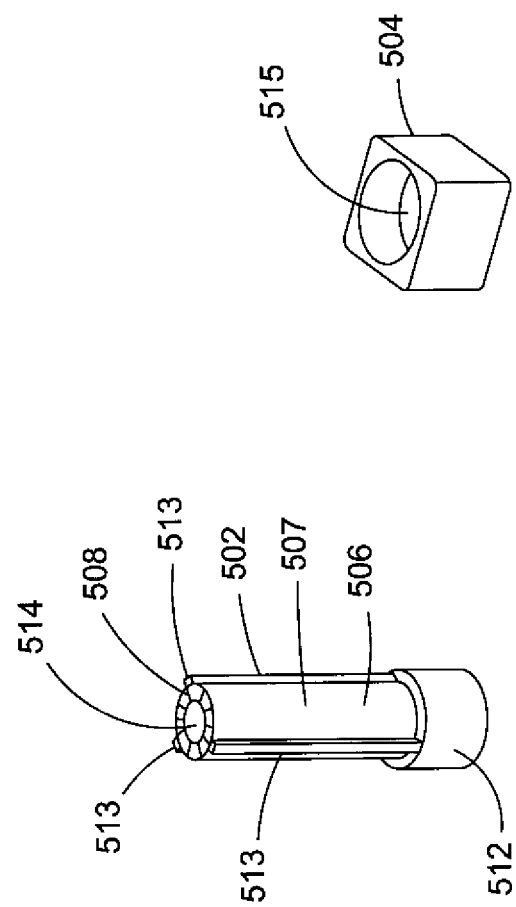
FIG. 5B
FIG. 5A

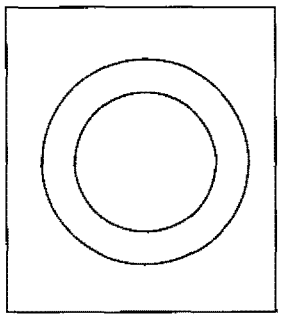
1141
No Tube
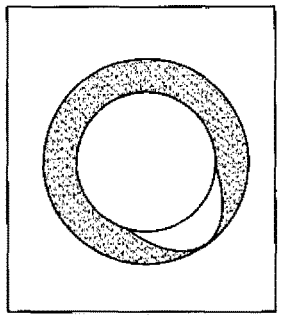
1142
Normal Priority Tube
Waiting for Processing
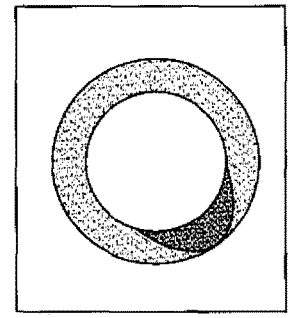
1146
STAT Priority Tube
Waiting for Processing
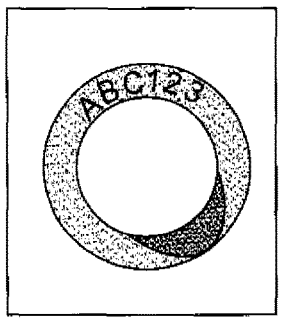
1147
STAT Priority Tube
w/Acc#"ABC123"
Waiting for Processing
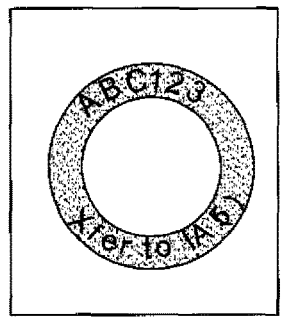
1148
Transfer Tube to
ImmunoAssay(IA)
Analyzer 5 to
continue processing
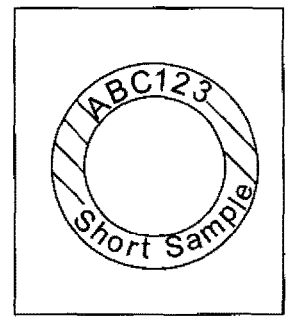
1149
Error-There is not
enough sample to run
all requested tests
1144
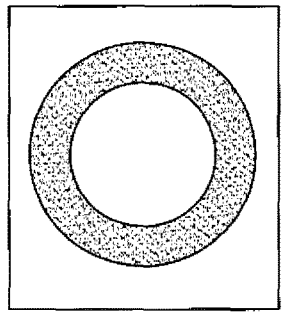 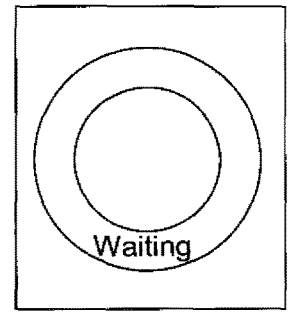
FIG. 11

MULTIPLE CARRIER AND SLEEVE TRAY

CROSS-REFERENCE TO RELATED APPLICATIONS

This application claims priority to U.S. provisional application Ser. No. 61/721,411 filed Nov. 1, 2012, which is incorporated herein by reference in its entirety.

TECHNOLOGY FIELD

The present invention relates in general to an automation system (e.g. a traditional Laboratory Automation System (LAS), and/or an integrated clinical instrument system that contains one or a plurality of stations, instruments, modules between which samples are moved by automation) for use in a laboratory environment and, more particularly, to systems and methods for transporting sample racks or pucks between an accessioning area and the automation system by utilizing devices, such as trays to quickly load and unload one or a plurality of racks and/or pucks to or from one or a plurality of loading/unloading areas that are an integral part of a clinical analyzer or an LAS.

BACKGROUND

In-vitro diagnostics (IVD) allows labs to assist in the diagnosis of disease based on assays performed on patient fluid samples. IVD includes various types of analytical tests and assays related to patient diagnosis and therapy that can be performed by analysis of a sample (e.g., liquid) taken from a patient's body, or abscesses. These assays are typically conducted with automated clinical chemistry analyzers (analyzers) onto which fluid containers, such as tubes or vials, containing patient samples have been loaded. The analyzer extracts a liquid sample from the vial or tube and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer), which may include immunoassay (IA) and clinical chemistry (CC) stations and/or pre and post analytical modules. Some traditional IVD automation track systems comprise systems that are designed to transport samples from one fully independent, standalone module to another fully independent, standalone module. This allows different types of tests to be specialized in two different stations or allows two redundant stations to be linked to increase the volume of sample throughput available.

In some conventional systems, individual carrier mechanisms (carriers), such as pucks and racks, and containers (e.g., test tubes) containing fluids, such as patient samples, are automatically shuttled between different stations. Typically, carriers remain on the track, regardless of whether they have a container associated with them. Separate from the track, (e.g., in other parts of the laboratory), containers may be stored in storage devices, such as racks (wired racks), plastic bins, trays, etc. The fluid containers are manually removed or picked from the storage devices and loaded into carriers/pucks, used to transport containers around the track, by an operator. The operator may also use a specially designed device to bring or remove one or a plurality of carriers at the same time. The process is reversed when the containers (tubes) have completed being processed by the instrument. Once processed, the fluid containers may also be manually unloaded from carriers and placed into temporary storage devices so they can be taken away from the system for further processing. This manual unloading and loading of the containers is labor intensive, requiring time and energy from the operator.

Some conventional systems use automated pick and place devices to load and unload the individual containers to and from temporary storage devices in an effort to reduce the time and energy required by manual unloading and loading. The pick and place devices load one or a plurality of test tubes at a time from temporary storage devices located within a storage area where they would have been placed by an operator. These pick and place devices can also unload containers from carriers located on the track and place them into temporary storage devices located within a storage load/unload area, associated with the instrument or LAS. Conventional systems that use automated pick and place devices may, however, be large, complex, and expensive. What is needed is an improved system for loading and/or unloading samples to and from the track.

SUMMARY

Embodiments of the present invention include an automation system for use with in-vitro diagnostics that includes a track configured to provide one or more paths and a plurality of sleeves. Each sleeve is configured to hold one of a plurality of fluid containers. The system also includes a plurality of carriers configured to travel along the track. Each carrier is separable from each sleeve and configured to hold one of the plurality of sleeves. The system further includes a tray having a plurality of rows. Each row is configured to hold at least one of: (i) one or more of the plurality of sleeves; and (ii) one or more of the plurality of carriers. The tray is configured to at least one of: (i) unload the one or more sleeves or unload the one or more carriers from the tray; and (ii) load the one or more sleeves or load the one or more carriers to the tray.

According to an embodiment, the automation system further includes a loading area configured to hold the one or more carriers and provide the one or more carriers access to the track. The tray is further configured to at least one of: (i) unload the one or more sleeves or unload the one or more carriers from the tray to the loading area; and (ii) load the one or more sleeves or load the one or more carriers from the loading area to the tray. According to an aspect of an embodiment, the track comprises the loading area.

According to another embodiment, the tray is further configured to at least one of: (i) unload the one or more sleeves or unload the one or more carriers through a bottom of the tray; and (ii) load the one or more sleeves or the one or more carriers through the bottom of the tray.

According to an aspect of an embodiment, the tray is further configured to at least one of: (i) unload each of the one or more sleeves or unload each of the one or more carriers substantially simultaneously from the tray; and (ii) load each of the one or more sleeves or load each of the one or more carriers substantially simultaneously to the tray.

According to one embodiment, the tray is further configured to at least one of: (i) unload the one or more sleeves or unload the one or more carriers through an edge of the tray; and (ii) load the one or more sleeves or load the one or more carriers through the edge of the tray.

According to another embodiment, the tray is further configured to at least one of: (i) unload a first row of the plurality of rows in parallel with a second row of the plurality of rows; and (ii) load the first row of the plurality of rows in parallel with the second row of the plurality of rows.

According to another embodiment, the tray is configured to at least one of: (i) unload a sleeve or a carrier from a first row of the plurality of rows substantially simultaneous with a sleeve or a carrier from a second row of the plurality of rows; and (ii) load the sleeve or the carrier from the first row of the plurality of rows substantially simultaneous with the sleeve or the carrier from the second row of the plurality of rows.

Embodiments of the present invention include an automation system for use with in-vitro diagnostics that includes a track configured to provide one or more paths and a plurality of carriers configured to travel along the track. Each carrier is configured to hold at least one of: (i) one or more of a plurality of fluid containers; and (ii) one or more of a plurality of sleeves. Each of the one or more sleeves is configured to hold the one or more fluid containers. The system also includes a tray having a plurality of rows. Each row is configured to hold one or more of the plurality of carriers. The tray is configured to at least one of: (i) perform a load-unload operation to one or more of the plurality of carriers through a bottom of the tray; and (ii) perform the load-unload operation to the one or more carriers through an edge of the tray.

Embodiments of the present invention include a tray for use with in-vitro diagnostics including a tray body having a plurality of rows, each row configured to hold at least one of: (i) one or more of a plurality sleeves; and (ii) one or more of a plurality of carriers. The tray body is configured to perform a load-unload operation using at least one of: (i) the plurality of sleeves; and (ii) the plurality of carriers. Each sleeve is configured to hold one of a plurality of fluid containers. Each carrier is separable from each sleeve and each carrier is configured to travel along a track and hold at least one of: (i) one of the plurality of sleeves; and (ii) one of the plurality of fluid containers.

According to one embodiment, the tray body is further configured to perform the load-unload operation through a bottom of the tray body.

According to another embodiment, the tray body is further configured to perform the load-unload operation through an edge of the tray body.

Embodiments of the present invention include a method for performing a load-unload operation in an in-vitro diagnostics system that includes receiving, into a plurality of rows of a tray, at least one of (i) a plurality of fluid container sleeves configured to hold a plurality of fluid containers; and (ii) a plurality of carriers, separable from and configured to hold the plurality of fluid container sleeves or the plurality of fluid containers and configured to travel along a track. The method also includes retaining, in the plurality of rows of the tray, the at least one of (i) the plurality of fluid container sleeves; and (ii) the plurality of carriers. The method further includes releasing, through a bottom of the tray, the at least one of (i) the plurality of fluid container sleeves; and (ii) the plurality of carriers.

According to one embodiment, the receiving further includes substantially simultaneously receiving the at least one of (i) the plurality of fluid container sleeves; and (ii) the plurality of carriers through the bottom of the tray.

According to another embodiment, the releasing further includes substantially simultaneously releasing the at least one of (i) the plurality of fluid container sleeves; and (ii) the plurality of carriers from the tray through the bottom of the tray.

According to another embodiment, retaining the least one of (i) the plurality of fluid container sleeves; and (ii) the plurality of carriers further includes applying a mechanical force to the least one of (i) the plurality of fluid container sleeves; and (ii) the plurality of carriers.

According to an aspect of an embodiment, retaining the least one of (i) the plurality of fluid container sleeves; and (ii) the plurality of carriers further in applying a magnetic force to the least one of (i) the plurality of fluid container sleeves; and (ii) the plurality of carriers.

According to another aspect of an embodiment, releasing the least one of (i) the plurality of fluid container sleeves; and (ii) the plurality of carriers further includes manually applying a force to substantially simultaneously release the least one of (i) the plurality of fluid container sleeves from the tray; and (ii) the plurality of carriers from the tray.

According to another embodiment, the method further includes sensing a location of the tray, and the releasing further includes substantially simultaneously releasing the at least one of (i) the plurality of fluid container sleeves from the tray; and (ii) the plurality of carriers from the tray responsive to the sensing the location of the tray.

Embodiments of the present invention include a method for performing a load-unload operation in an in-vitro diagnostics system that includes receiving, into a plurality of rows of an edge loading tray, a plurality of carriers configured to hold a plurality of fluid container sleeves and configured to travel along a track. The method also includes retaining the plurality of carriers in the plurality of rows of the edge loading tray and releasing the plurality of carriers through an edge of the edge loading tray.

According to an embodiment, the releasing further includes releasing a first row of the plurality of rows in parallel with a second row of the plurality of rows.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIGS. 2A and 2B are diagrammatic views of track geometries that can be used with the automation system embodiments disclosed herein;

FIG. 4A is a perspective view of an exemplary carrier, with an exemplary fluid container that can be used with the embodiments disclosed herein;

FIGS. 5A through 5F are perspective views of a sleeve, carrier, and fluid container at different states that can be used with the embodiments disclosed herein;

FIG. 11 is a diagrammatic view of multiple exemplary states of electronically rewritable surfaces for displaying status information about a sample;

DETAILED DESCRIPTION OF ILLUSTRATIVE EMBODIMENTS

Figure 1:
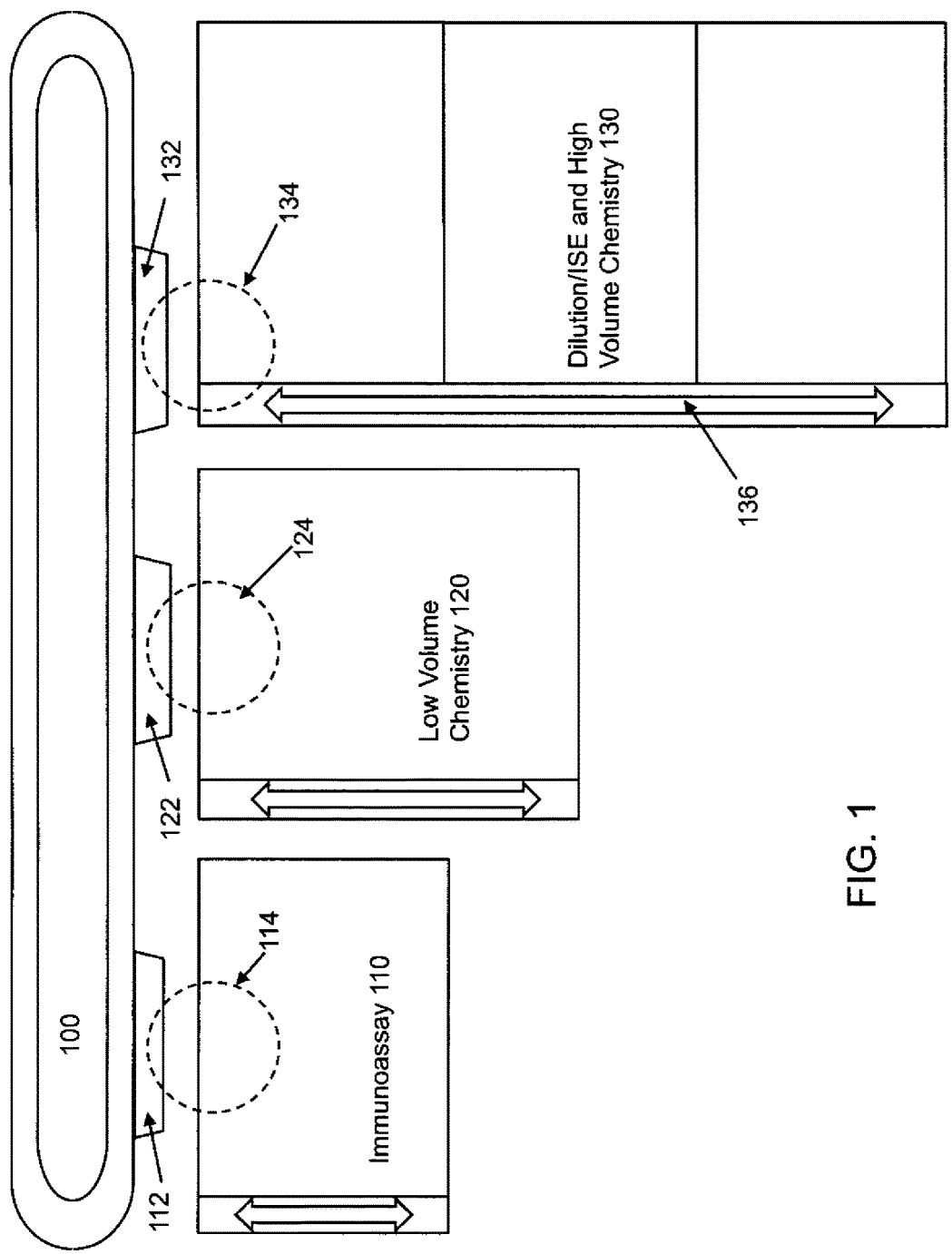
FIG. 1 is a top view of an exemplary clinical analyzer geometry that can be improved by use of the automation system embodiments disclosed.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers, are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes maximum jerk, acceleration, direction, and/or speed for the carrier while moving in the automation system. The motion profile can limit or define the trajectory for each carrier independently. In some embodiments, a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. IVD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Embodiments of the present invention include systems and methods that provide a more efficient lab automation system for moving sample carriers between various modular testing stations by utilizing trays that can quickly load and unload a plurality of carriers and/or sleeves to and from the trays to a track. Embodiments of the present invention include systems and methods that provide a more efficient lab automation system for loading and/or unloading samples to and from the track without the need for a pick and place mechanism. Embodiments of the present invention include bottom loading trays that may substantially simultaneously load and unload carriers and/or sleeves through bottoms of the bottom loading trays. Embodiments of the present invention include edge loading trays that may load and unload rows of carriers and/or sleeves in parallel through edges of the edge loading trays.

Exemplary Modular Automation System for Use with Carriers

An exemplary track geometry for use in transporting samples within an analyzer typical in prior art configurations is shown in FIG. 1. This track can include prior art friction tracks, which may introduce problems in designing a track system. However, certain embodiments of the present invention could also use a similar geometry without necessarily employing a friction track for motion. Track 100 can be a generally oval-shaped track that conveys samples in pucks or trays between various stations, such as sample preparation or analyzing/testing stations 110, 120, and 130. Track 100 could be a single direction track or, in some instances, a linear bidirectional track. In this exemplary set-up, each analyzer 110, 120, 130 is serviced by a respective sidecar 112, 122, 132. At the junction between the track 100 and each sidecar, a gate or switch can be placed that allows samples to be diverted to or from track 100 to the sidecar. The oval nature of track 100 can be used to circulate samples while they wait for access to each analyzer. For example, analyzer 110 may have a full queue in sidecar 112, such that new samples on track 100 cannot be diverted to pullout 112 until analyzer 110 finishes handling a pending sample in sidecar 112 and inserts it back into the main traffic flow of track 100.

In some prior art systems, each sidecar can be serviced by a handling mechanism such as sample probe arms 114, 124, and 134. These robotic handling arms can aspirate sample material from samples in a sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry station or (stations) 130. Some advantages of this approach are that the track 100 can be part of a separate lab automation system that can be added onto otherwise self-contained stations, and the track 100 and stations 110, 120, and 130 can be independently upgraded, purchased, or serviced. Some stations, such as high-volume chemistry station 130, can include their own friction track 136 that operates independently of track 100. Friction track 136 can include a bidirectional friction track that allows samples to move between sub-modules of high-volume chemistry station 130. A drawback of this type of system is that the separate friction tracks operate independently and control of overall automation becomes more complicated. Furthermore, transitions between friction tracks 136 and 100 can be slow and cumbersome, particularly where there is no direct route between two friction tracks. In some systems, moving between tracks may require lifting and placing samples via a robot arm.

Prior art lab automation systems for analyzers generally treat individual analyzer/testing stations as generic destinations for a sample on the track. In some embodiments of the present invention, the lab automation system can be integrated within the individual testing stations, which can substantially reduce or eliminate the complexity of the individual testing stations and reduce the need for separate sample handling systems within each station. In some embodiments, by integrating the lab automation system into the stations, the system can begin to treat individual stations less as generic destinations and more as portions of a multi-route track onto which a sample can travel.

FIG. 2A shows one embodiment of a track system that can be adapted for use with the present invention. Track 150 is a rectangular/oval/circular track on which sample carriers move in a clockwise (or counterclockwise) direction. Track 150 may be unidirectional or bidirectional. Carriers can transport any suitable payload within an IVD environment, such as fluid samples, reagents, or waste. Fluids, such as patient samples, can be placed in a container or vessel, such as a test tube, vial, cuvette, etc. that can be transported by a carrier. Carriers and, by extension, payloads such as samples, can move on the main track 150 or be diverted via decision points such as 164 or 166. These decision points can be mechanical gates (as in the prior art) or other mechanisms suitable for allowing a sample to be diverted from the main track 150 to a sidecar, such as 160, 160A, 160B, 160C as described herein. By way of example, if a sample carrier is traversing the main path 150 and reaches decision point 166, it can be made to continue on the main track to segment 162 or it can be made to divert to sidecar 160. The systems and methods by which the decision can be made to divert the sample carrier at decision point 166 are described throughout.

FIG. 2B shows an alternative track layout that may be suitable for certain embodiments of the present invention. Track 170 is also a generally circular track with sample carriers moving (clockwise or counterclockwise). In this example, rather than having sidecars outside of the track, pullouts 180, 180A, and 180B are chords within the track. Similarly, when sample carriers reach decision points, they may be diverted off of the main path to a side path such as path 180. At decision point 186, a sample on the main track 170 can be made to continue on the main track or be diverted onto path 180. Once an analyzer station along handling path 180 is done processing the sample, the sample proceeds to decision point 184 where it may be placed back onto the main path 170.

Figure 3:
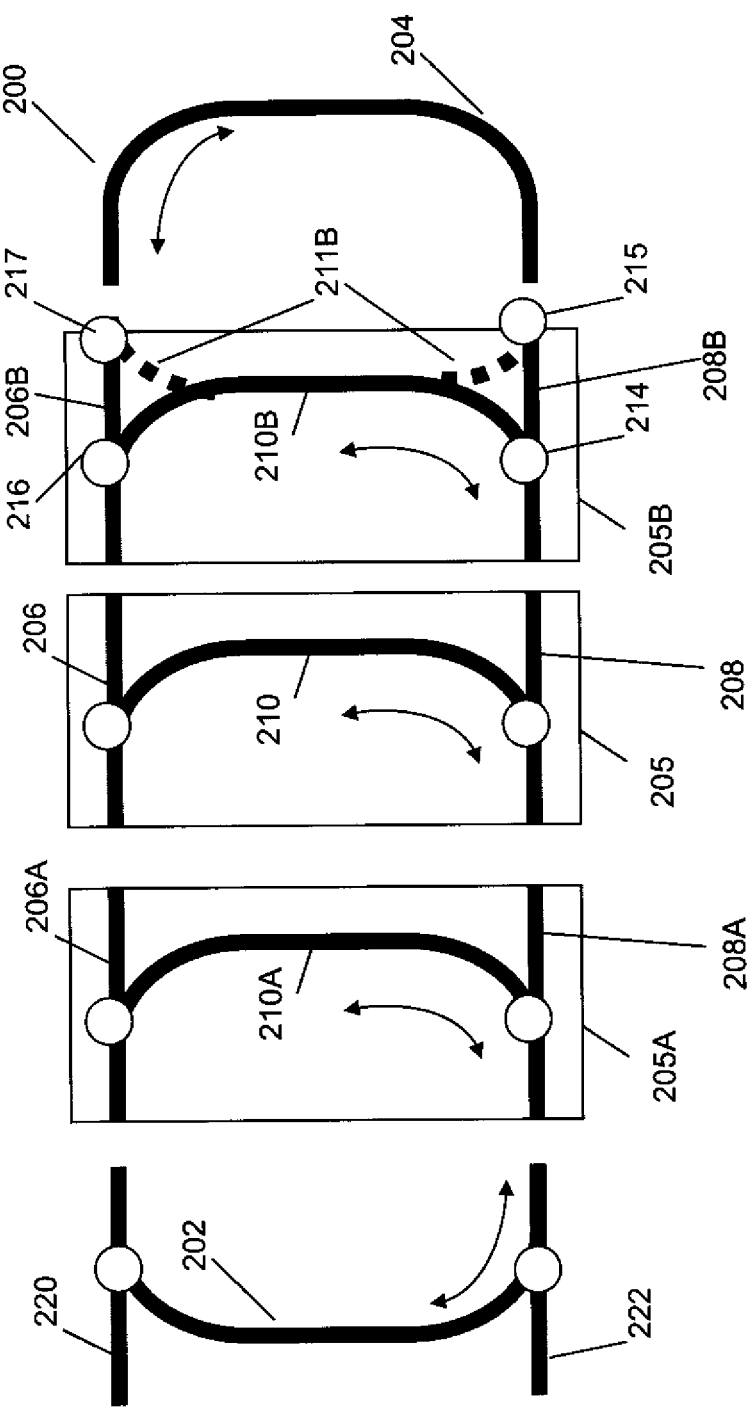
FIG. 3 is a diagrammatic view of an exemplary modular track configuration that can be used with the embodiments disclosed herein.

FIG. 3 shows a modular approach to the automation system track that can be used for certain embodiments of the present invention. In this example, the tracks may be integrated into individual analyzer stations, such that the track can be used as part of the internal motion or sample handling system of individual lab stations. In the prior art, it is common to have multiple different types of motion systems within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed. In some embodiments, by integrating portions of the track system into the analyzer stations themselves, each station can include its own queuing logic and may be simplified to eliminate unnecessary internal motion systems.

With respect to FIG. 3, the track 200 can be broken into modular components that are integrated into analyzer modules. In this exemplary track, modules 205, 205A, and 205B can be combined with one another and optionally other modular track components 202 and 204 to form a track similar to that shown in FIG. 2B. For instance, 205A can be a module that performs the same function as immunoassay 110 (FIG. 1), 205 can be a module that performs the same function as low-volume chemistry module 120 (FIG. 1), and 205B can be a module that performs ISE electrolyte testing, like module 130 (FIG. 1). In this example, the main outer track can be formed by track segments 202, 204, 206, 206A, 206B, 208, 208A, and 208B. Within the analyzer modules 205, 205A, and 205B, internal paths 210, 210A, and 210B form pullouts from the main track. The internal paths can be used for internal queuing and can be managed independently within each analyzer module to allow each module to have greater control over samples to be processed.

One advantage of integrating track 200 and sub-paths 210, 210A, and 210B into the analyzer modules 205, 205A, and 205B, respectively, is that the internal handling mechanisms within each analyzer module can be specially adapted to better coordinate with the track sub-paths. In some embodiments, modules 205, 205A, and 205B can be adapted to process each sample within a period that is less than an operation cycle of the overall analyzer, leaving enough time for the sample to be routed along the track system to another module after processing, allowing the other module to immediately process the sample on the next operation cycle. As used herein, an operation cycle is a unit of time used by scheduling algorithms to allot processing time to modules for sample assays. These can be dynamic or fixed and can allow synchronous operation of the modules in the analyzer and provide a reliable timing model for scheduling samples amongst multiple modules in the analyzer. The operation cycle time can be chosen to be the time needed by any given module between when it starts processing a first sample, and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle, to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle times or demand vary between modules.

Enabling transit between modules in the analyzer in a reliable time frame, on the order of a single operation cycle or less, achieves many performance advantages not possible with prior art track systems. If a sample can be reliably handled by an analyzer module and transported to the next analyzer module within a single cycle of the analyzer, traffic handling in queuing becomes much simpler, throughput becomes more consistent, and latency can be controlled and reduced. Essentially, in such an analyzer, a sample can reliably be handled by the track system and processed uniformly such that a sample does not sit idly on the track system waiting in queues. Furthermore, queues within the system, such as queues within a given analyzer module, can reliably be shortened, limited by the number of modules within the system.

In some embodiments of the present invention, the reliable and rapid nature of the track system enables queues to be virtual, rather than physical. A virtual queue can be handled in software, rather than by physical limitations. Traditionally, queues have been physical. The simplest physical queue is effectively a traffic jam at any given part of a sample handling operation. A bottleneck creates a first-in first-out (FIFO) queue, where sample carriers are effectively stopped in a line, providing a buffer so that an analyzer or a decision point can request the next sample in the queue when it is ready. Most prior art lab automation tracks maintain FIFO processing queues to buffer samples that are waiting to be processed by the attached modules (analyzers or pre/post analytic devices). These buffers allow the track to process sample tubes at a constant rate, even though the modules or operator requests can create bursts of demand. FIFO queues can also substantially increase the throughput of the individual modules by allowing them to perform preprocessing tasks for future samples, for example, prepare a cuvette or aspirate reagent, while processing the current sample. While the rigid predictability of FIFO queues enables the parallelization of some processing tasks, it also can prevent the modules from using opportunistic scheduling that may increase throughput by reordering tests on samples to optimize resources. For example, the internal resource conflicts of most immunoassay analyzers can be so complex that the analyzers need to interleave the tests from multiple samples in order to reach maximum efficiency. A FIFO queue can reduce the throughput of these analyzers by as much as 20%. Another challenge with FIFO queues is their inability to handle priority samples (e.g., a STAT sample). If a STAT sample needs to be processed immediately, the entire FIFO queue has to be flushed back onto the main track, delaying all other samples on the track and forcing the original module to slowly rebuild its queue.

Another type of queue is a random access (RA) queue. A carousel is an example of a physical RA queue found in analyzer modules. By aliquoting a portion of a sample into one or more vessels in a carousel ring, an analyzer module can select any of a number of samples to process at any time within the analyzer. However, carousels have many drawbacks, including added complexity, size, and cost. A carousel also increases the steady-state processing time, because a sample must be transferred into and out of the random-access queue. Processing delays depend on the implementation, such as the number of positions in a carousel. On the other hand, by having random access to samples, a local scheduling mechanism within a module can process samples in parallel, performing sub-steps in any order it desires.

In some embodiments, carousels or other RA queues can be eliminated from the modules and the sub-paths (e.g., 210) from the automation system can be used as part of an RA or FIFO queue. That is, if the travel time for a sample between any two points can be bounded to a known time that is similar to that of a carousel, such as predictably less than a portion of an operation cycle, the track 200 can be part of the queue for a given module. For example, rather than using a carousel, module 205 can utilize samples in carriers on sub-path 210. Preprocessing steps, such as reagent preparation, can be conducted prior to the arrival of a sample under test. Once that sample under test arrives, one or more portions of the sample can be aspirated into cuvettes or other reaction vessels for an assay. In some embodiments, these reaction vessels can be contained within module 205, off track, while in other embodiments, these reaction vessels can be placed in carriers on sub-path 210 to allow easy motion. If the sample under test is required to be at a module for longer than an operation cycle, or if multiple samples will be processed by the module during an operation cycle, the sub-path 210 can act as a queue for the module.

Furthermore, samples not yet under test, which may be currently located at other modules, can be scheduled for the next operation cycle. These next-cycle samples can be considered as residing in a virtual queue for module 205. A module can schedule samples to arrive during a given operation cycle for any sample on track 200. A central controller, or controllers associated with modules themselves, can resolve any conflicts over a sample for a given cycle. By giving a module a prior knowledge of the arrival time of a sample, each module can prepare resources and interleave tests or portions of tests to more efficiently allot internal resources. In this manner, modules can operate on samples in a just-in-time manner, rather than by using large physical buffers. The effect is that the virtual queue for a given module can be much larger than the physical capacity of the sub-path serving that module, and existing scheduling algorithms can be used. Effectively, each module can treat track 200 as it would treat a sample carousel in a prior art module.

It should be appreciated that, by employing virtual queues in some embodiments, multiple modules can have multiple queues and can share a single queue or samples within a queue. For example, if two modules are equipped to perform a certain assay, a sample needing that assay can be assigned to a virtual queue for that assay, which is shared between the two modules capable of handling the assay. This allows load balancing between modules and can facilitate parallelism. In embodiments where reaction vessels are placed in carriers on track 200, an assay can be started at one module (e.g., reagents prepared and/or sample mixed in) and the assay can be completed at another (e.g., a reaction is observed at another module). Multiple modules can effectively be thought of as a multi-core processor for handling samples in some embodiments. In these embodiments, scheduling algorithms for the multiple modules should be coordinated to avoid conflicts for samples during a given operation cycle.

By employing virtual queues, modules can operate on samples while the samples are in the virtual queues of other modules. This allows low latency of samples, as each sample that is placed onto track 200 can be processed as quickly as the modules can complete the tests, without having to wait through a physical queue. This can greatly reduce the number of sample carriers on track 200 at any given time, allowing reliable throughput. By allowing modules to share queues or samples, load balancing can also be used to maximize throughput of the system.

Another advantage of using virtual queues is that STAT samples can be dynamically assigned priority. For example, a STAT sample can be moved to the head of any queue for the next operation cycle in software, rather than having to use a physical bypass to leapfrog a STAT sample to the head of a largely static physical queue. For example, if a module is expecting three samples to be delivered by track 200 for assays during the next operation cycle, a scheduler responsible for assigning samples to the module can simply replace one or more of the samples with the STAT sample, and have the track 200 deliver the STAT sample for processing during the next operation cycle.

If decision points such as 214 and 216 can be streamlined such that there is no need for a queue at each decision point, the only physical queues can be within sub-paths 210, 210A, and 210B. As described above, these can be treated as RA queues or FIFO queues. If a STAT sample is placed onto track 200, RA queues within sub-paths 210, 210A, and 210B need not be flushed, as the STAT sample can be processed immediately. Any FIFO queues can be individually flushed. For example, if a STAT sample is placed onto track 200 at section 222, the sample may be routed to the appropriate analyzer 205B via the outside track and decision point 216. If there are other samples (and, by extension, the sample carriers transporting those samples) waiting in the queue in path 210B, only those samples in the queue may need to be flushed to allow a STAT sample to take priority. If the outer track 200 is presumed to take less than an operation cycle to traverse, any samples that were flushed from the queue in 210B can simply be circulated around the track and placed immediately back into the queue in path 210B immediately behind the STAT sample, eliminating any down time caused by the STAT sample.

Entry paths 220 and 222 can be used to input samples to the track 200. For example, regular priority samples can be placed onto track 200 at input 220 and STAT priority samples can be placed on input 222. These inputs can be used as outputs for samples when complete, or other ports (not shown) can be used as the output paths for used samples. Input 220 can be implemented as an input buffer, acting as a FIFO queue for input samples seeking access to the track 200. Once a sample reaches the head of the queue at input 220, it can be moved onto the track (either by being placed in a carrier or by being placed in a carrier when it is placed in input 220). A STAT sample can enter the track 200 immediately after being placed at input 222 or, if track 200 is overcrowded, the STAT sample can enter the track at the next available uncrowded operation cycle. Some embodiments monitor the number of carriers on the track during an operation cycle and limit the total number to a manageable amount, leaving the remainder in input queues. By restricting samples at the input, track 200 can be free of traffic, allowing it to always be operated in the most efficient manner possible. In these embodiments, the transit time of a sample between two modules can be a bounded value (e.g., less than some portion of an operation cycle), allowing simplified scheduling.

In some embodiments, the track system 200 can be designed to be bidirectional. This means that sample carriers can traverse the outside path and/or any sub-paths in either direction. In some embodiments, additional sub-paths, such as 211B accessed via additional decision points 215 and 217, can assist in providing bidirectional access. Bidirectional paths can have inherent advantages. For example, if normal priority samples are always handled in the same direction, a STAT sample can be handled in the opposite direction along the sub-path. This means that a STAT sample can essentially enter the exit of the sub-path and be immediately placed at the head of the queue without requiring the queue to be flushed. For example, if a STAT sample is placed on track 200 at segment 204, it can enter path 210B via decision point 214 and proceed into path 210B to be immediately placed at the head of any queue. Meanwhile, in all of these examples, because queues are presumed to be limited generally to sub-paths, there is no need to flush queues in other modules if a STAT sample does not need immediate access to those modules. Any additional modules that need to service a STAT sample on a subsequent cycle can flush their queues at that point, providing "just-in-time" access to a STAT sample without otherwise disrupting the operation of each analyzer module.

Modular design also allows certain other advantages. If the automation systems within an analyzer module are adapted to take advantage of the track system contained in the module, new features can be added that use the common track. For example, a module could have its own internal reagent carousel that includes all of the reagents necessary for performing the assays prescribed for the samples. When reagents stocked in the analyzer module run low, an operator can replenish the reagents in some embodiments by simply loading additional reagents onto the carriers on track 200. When the reagents on track 200 reach the appropriate module, the module can utilize mechanical systems such as an arm or a feeder system that takes the reagents off of the track and places the reagents in the reagents store for the module.

In some embodiments, the individual track portions shown in FIG. 3 and FIGS. 2A and 2B can be operated independently from one another, or can be passive. Independent carrier movement provides advantages over friction-based track systems, such as non-localized conveyor belts where the entire friction track must be moved to effect movement of a sample carrier. This means that other samples also on that track must move at the same rate. This also means that if certain sections operate at different speeds, collisions between passive carriers carrying samples can occur.

FIG. 4A depicts an exemplary carrier 250 for use with some embodiments of the present invention. Carrier 250 can hold different containers or payloads in different embodiments. One type of container or payload can be a sample tube 255, which contains a fluid sample 256, such as blood or urine. Other payloads may include racks of tubes or reagent cartridges, or any other suitable cartridges. Sample carrier 250 includes a main body 260, which can house the internal electronic components described herein. The main body 260 supports a bracket 262, which can accept a payload. In some embodiments, this is a shallow hole that is designed to accept a fluid container 255 such as a sample tube, and hold it with a friction fit. In some embodiments, the friction fit can be made using an elastic bore or a clamp that can be fixed or energized with a spring to create a holding force. In some embodiments, sample racks and reagent cartridges can be designed to also attach to the bracket 262, allowing bracket 262 to act as a universal base for multiple payload types. In the exemplary embodiment shown in FIG. 4A, bracket 262 is round. In other embodiments may include other mounting interfaces of any shape and size configured to accept and/or hold a payload.

Body 260 can include or be coupled to guide portion 266, which allows the carrier 250 to follow a track between decision points. Guide portion 266 can include, for example, a slot to accept one or more rails in the track, providing lateral and/or vertical support. In some embodiments, the guide portion allows the carrier 250 to be guided by walls in the track, such as the walls of a trough-shaped track. The guide portion 266 can also include drive mechanisms, such as friction wheels that allow a motor in the carrier body 260 to drive the carrier or puck 250 forward or backward on the track. The guide portion 266 can include other drive components suitable for use with the embodiments described throughout, such as magnets or induction coils. In some embodiments, main housing 260 may be a solid block without guide portion 266.

Rewritable display 268 can be provided on the top of the carrier 250. In other embodiments a rewritable display may be on the top surface of bracket 262. In other embodiments, the rewritable display may be on the top surface 508 and/or any exterior facing surface of the sleeve 502. In still another embodiment, a rewritable display may be any combination of locations of surfaces on 268, 262, 502, and/or 508. This display can include an LCD oriented panel and can be updated in real time by the carrier 250 or the main computer system via a wired and/or wireless signal so as to display status information about sample 256. By providing the electronically rewritable display on the top of the carrier 250, the status information can be viewed at a glance by an operator. This can allow an operator to quickly determine which sample he/she is looking for when there are multiple carriers 250 in a group. By placing the rewritable display on top of the carrier 250, an operator can determine status information even when multiple carriers 250 are in a drawer or rack. In some embodiments, the rewriteable display 268 may include a low powered and/or bi-stable material, which maintains the image over long period of time, without power. The information displayed on rewriteable display 268 may be received via a wireless signal.

Figure 4B:
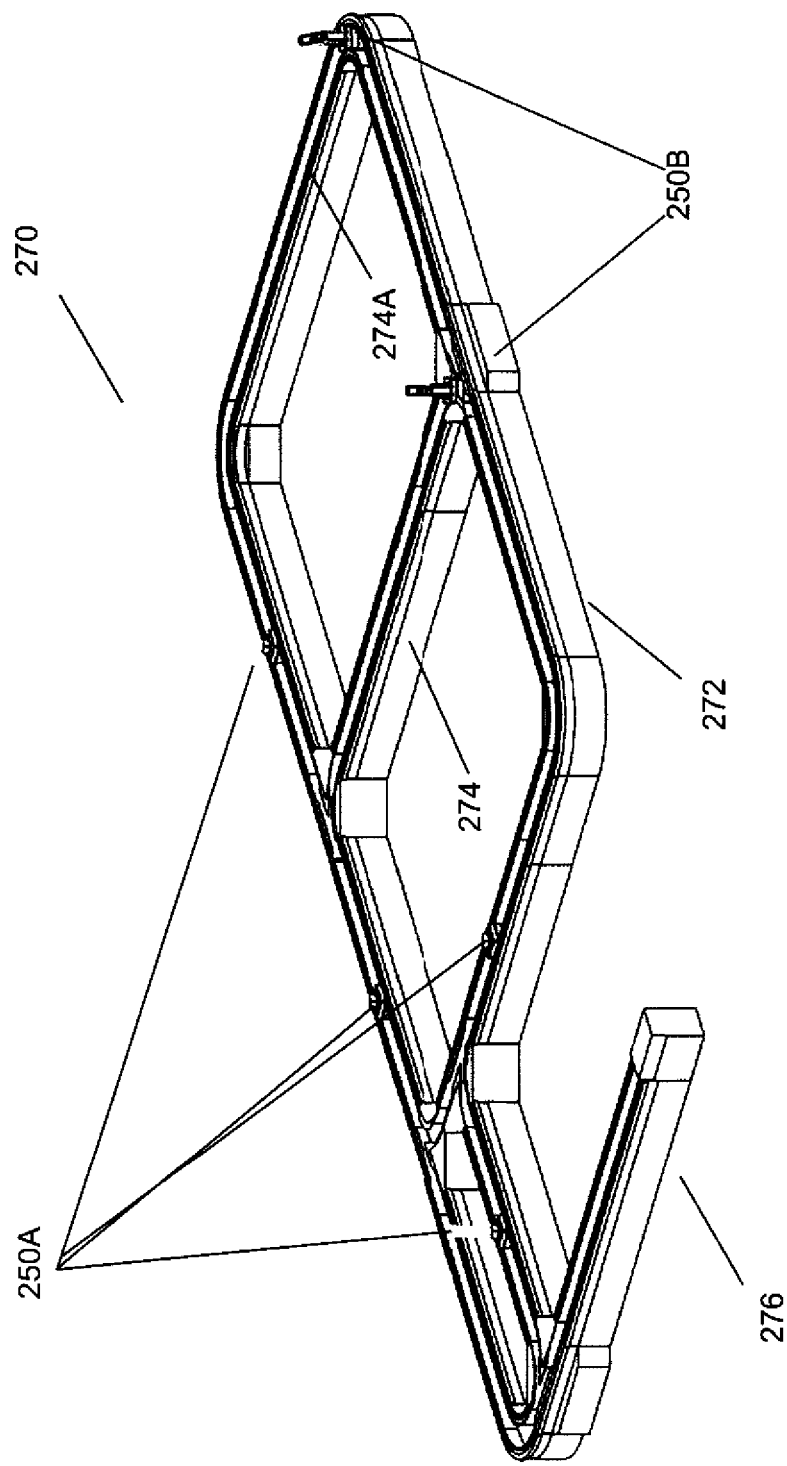
FIG. 4B is a perspective view of an exemplary track configuration that can be used with the embodiments disclosed herein.

FIG. 4B shows an exemplary track configuration 270 for use by carriers 250. In this example, carriers 250A transport sample tubes, while carriers 250B transport sleeves 502 and/or racks of tubes, and/or reagent cartridges along main track 272 and/or subpaths 274 and 274A. Path 276 can include a tray loading/unloading area by which may be used by an operator to place samples into carriers or remove samples from these carriers.

Figure 4C:
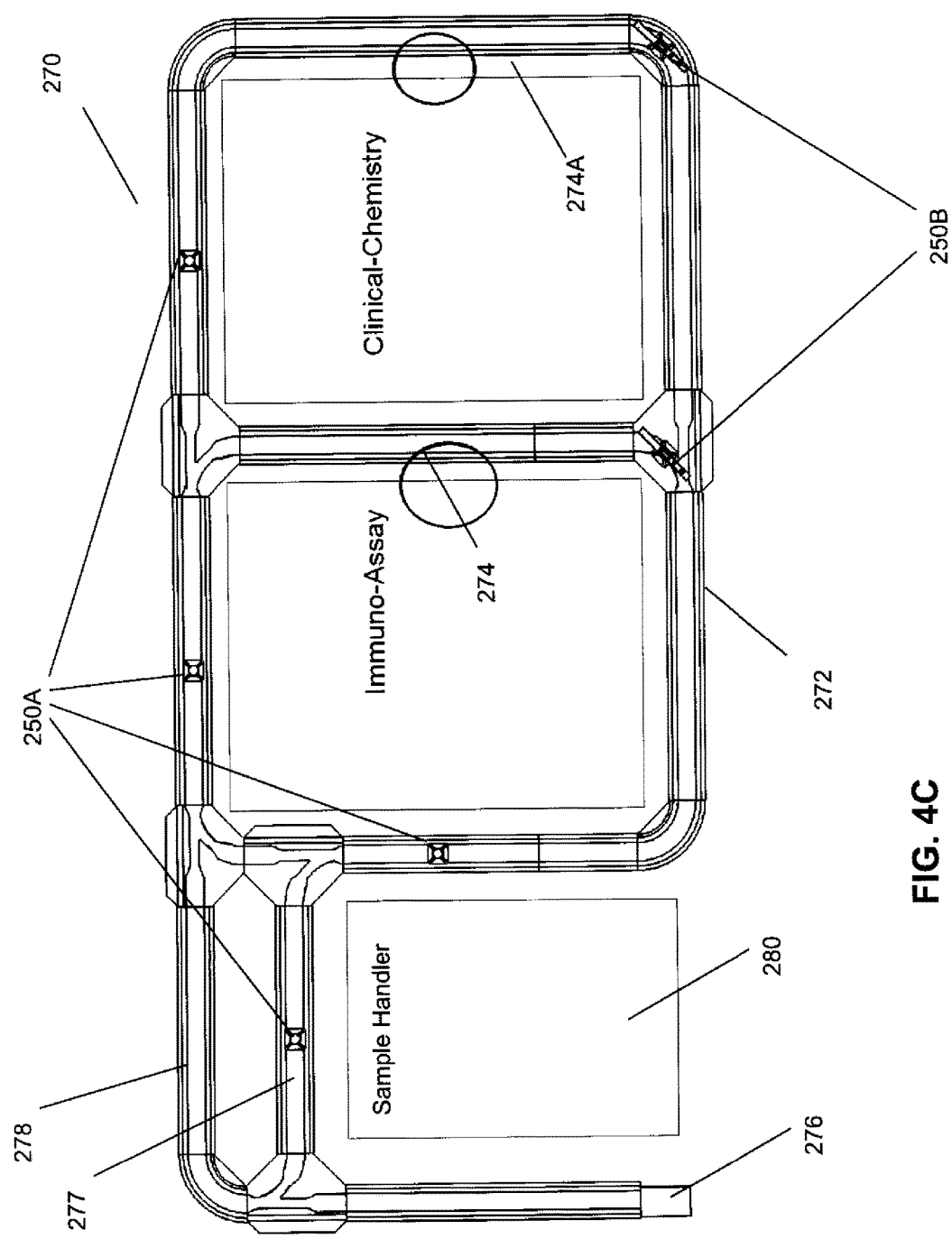
FIG. 4C is a top view of an exemplary automation system that can be used with the embodiments disclosed herein.

FIG. 4C shows an additional view of an exemplary track configuration 270. In this example, sub-path 274 serves an immunoassay station, while sub-path 274A serves a clinical chemistry station. Input/output lane 276 can be served by a sample handler station 280 that uses sub paths 277 and 278 to buffer samples for insertion or removal of the samples from the main track 272.

In some embodiments, the sample handler 280 may, for example via a pick and place mechanism, can also load and unload samples or other payloads to/from the carriers 250A and 250B. This allows the number of carriers to be reduced to the amount needed to support payloads that are currently being used by the stations in track system 270, rather than having a vast majority of carriers sitting idle on tracks 277 and 278 during peak demand for the analyzer. Instead, sample trays (without the carriers disclosed herein) can be placed/removed by an operator at input/output lane 276. This can reduce the overall cost of the system and the number of carriers needed can be determined by the throughput of the analyzer, rather than based on anticipating the peak demand for the analyzer in excess of throughput.

Exemplary Carrier Trays and Separable Sleeve Trays

As described above, some conventional systems may require an operator to manually remove or pick fluid containers from the racks and/or pucks on the track and load the fluid containers into laboratory temporary storage devices, which may then be physically placed at a location (e.g. on a bench top) separate or remote from the system. Operators may also manually unload the fluid containers from the temporary storage devices and place the fluid containers into racks and/or pucks on the track for transport between stations in an analyzer. This manual unloading and loading of the containers one at a time may be labor intensive. In an effort to reduce the time and energy required by manual unloading and loading, some conventional systems use automated pick and place mechanisms to load and unload the individual containers to and from the carriers, resulting in large, complex and expensive systems.

Embodiments of the invention include improved systems and methods for efficiently loading and unloading a larger number of fluid containers to and from the track by including carrier trays and/or separable fluid container sleeve trays configured for loading and unloading a plurality of carriers, and/or fluid containers, and/or sleeves to and from the track.

FIGS. 5A-5E are perspective views of an exemplary sleeve 502, carrier 504 and fluid container 510 shown at different states of assembly that can be used with the embodiments disclosed herein. As shown in FIG. 5A, sleeve 502 includes a sleeve body 506, a base portion 512, and ribs 513. The sleeve body 506 may include a hole 514 configured to engage the fluid container 510. As shown in FIG. 5 B, carrier 504 may include a slot 515. The slot 515 in carrier 504 may also be configured to engage base portion 512 and/or engage the fluid container 510. In some embodiments, sleeve 502 and carrier 504 may be manufactured as a single item. In some embodiments, hole 514 may be configured to cause the sleeve body 506 to engage the fluid container 510.

Figure 5F:
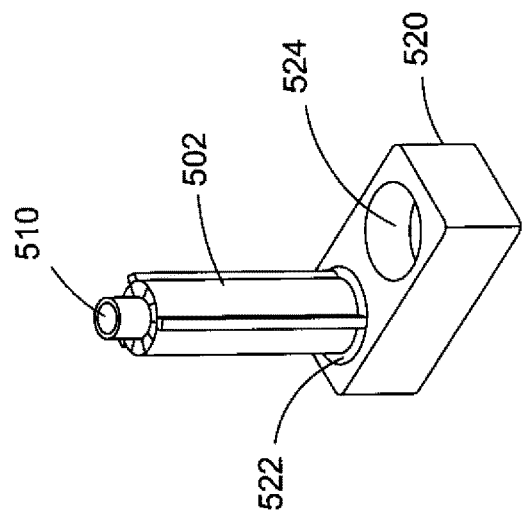
Figure 5E:
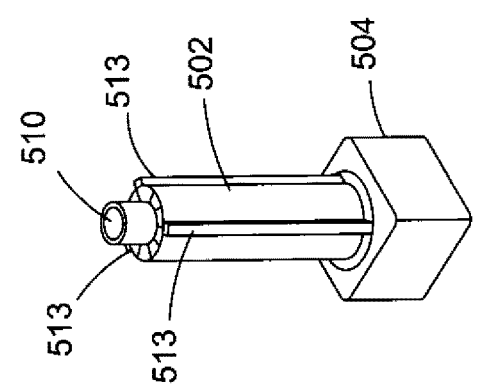
Figure 5D:
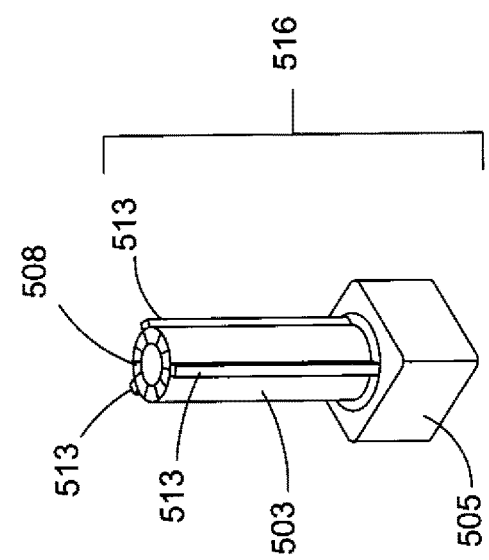

As shown in FIGS. 5A-5E, sleeve body 506 may also include ribs 513 disposed on an outer surface 507 of the sleeve body 506, spaced from each other and extending lengthwise from the top to the bottom of the sleeve body 506. In some embodiments, one or a plurality of ribs, such as ribs 513, may be coupled to or integral with sleeve body 506, which may provide a variety of features, such as portion for the operator to grasp. Ribs 513 may be configured to mount one or more electro-optical type externally facing devices (e.g., LCD and/or bi stable displays) or internally facing electro-optical type devices (e.g., LED and or CCD arrays), which may be used to read bar codes (such as bar codes on container 510 in hole 514 (shown in FIG. 5E) or to detect the quality and attributes of a sample in the container 510. The sleeve body 506 also includes a base portion 512 configured to engage carrier 504, which is configured to hold sleeve 502 and to travel along a track, such as track 200 shown in FIG. 3. As shown in FIGS. 5A, 5D, and 5E, ribs 513 may be disposed on an outer surface of sleeve body 506. In some embodiments (not shown), ribs 513 may be disposed on the sides of base portion 512. In some embodiments, the sleeve 502 is separable from carrier 504, as shown in FIG. 5C. In other embodiments, a single non-separable carrier 516 may include a sleeve portion 503 and a carrier portion 505, as shown in FIG. 5D. Sleeve 502 may also include an electronically rewriteable display 508 configured to display status information, as described in more detail below.

Embodiments of the present invention may also include multiple slot carriers 520. For example, as shown in FIG. 5F, multiple slot carrier 520 may include a plurality of slots 522 and 524. Slots 522 and 524 may be configured to engage fluid container 510 and/or sleeve 502. Aspects may include any number of slots each configured to engage base portion 512 and/or engage the fluid container 510. One or more algorithms may be used by a central controller (not shown) or an onboard controller, such as controller 1401 in FIG. 14, to control the placing and removal of sleeves 502 and/or fluid containers 510 in slots 522 and 524. In some aspects, one or more controllers may control the multiple slot carrier 520 to have at least one empty slot 524 at any location on track 200.

The size and shape of the carriers 504, 516, and 520, sleeve 502, and fluid container 510 in the embodiments shown in FIG. 5A to FIG. 5E are exemplary. Embodiments may include carriers, sleeves and/or fluid containers having other sizes and shapes.

Figure 6B:
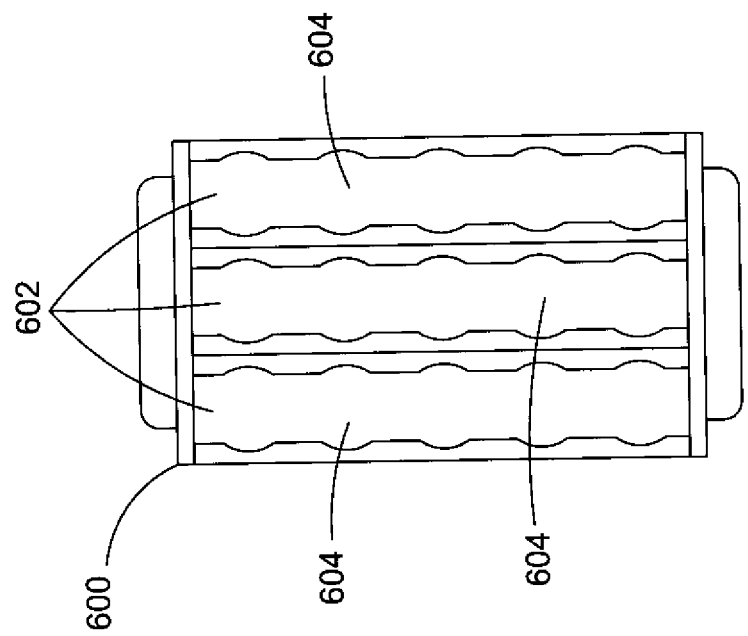
FIG. 6B is a top view of the exemplary bottom loading tray shown in FIG. 6A that can be used with the embodiments disclosed herein.
Figure 6A:
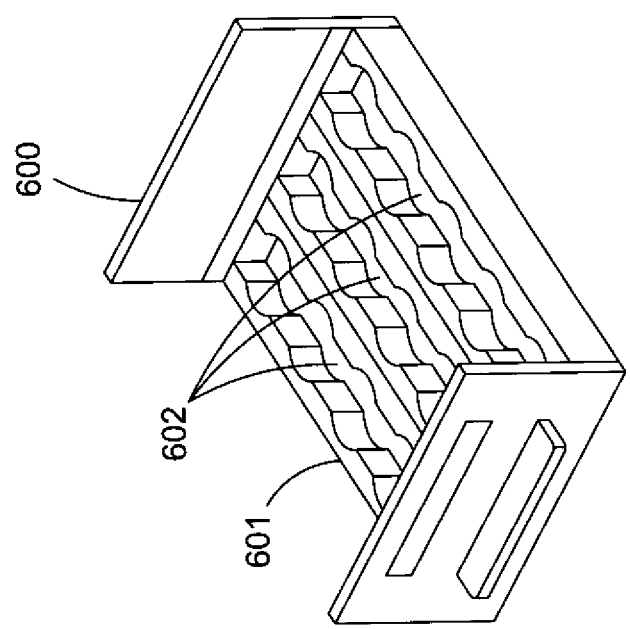
FIG. 6A is a perspective view of an exemplary bottom loading tray for holding a plurality of sleeves or carriers that can be used with the embodiments disclosed herein.
Figure 6D:
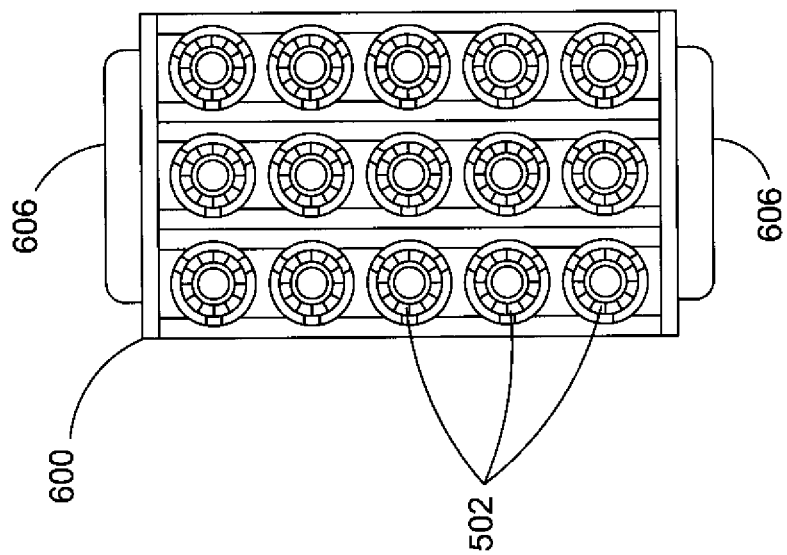
FIG. 6D is a top view of the exemplary bottom loading tray shown in FIG. 6C holding a plurality of exemplary sleeves holding fluid containers that can be used with the embodiments disclosed herein.
Figure 6C:
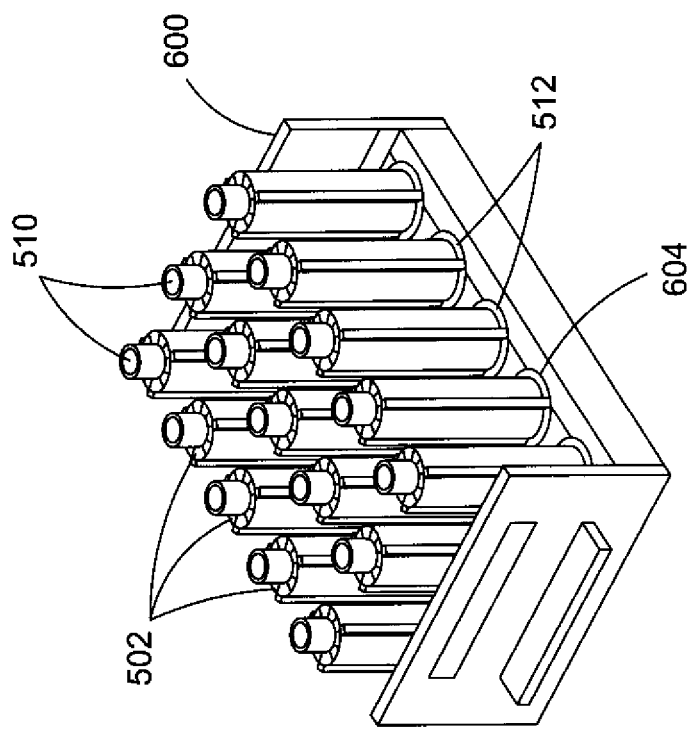
FIG. 6C is a perspective view of the exemplary bottom loading tray shown in FIG. 6A holding a plurality of exemplary sleeves holding fluid containers that can be used with the embodiments disclosed herein.

In some embodiments, carriers 504 and/or sleeves 502 may be bottom loaded. FIG. 6A is a perspective view of an exemplary bottom loading tray 600 for holding a plurality of sleeves 502 that can be used with the embodiments disclosed herein. As shown in FIG. 6A and FIG. 6B, tray 600 may include a tray body 601. Tray body 601 includes a plurality of rows 602. Each row 602 may be configured to hold one or more sleeves 502. Each sleeve may be configured to hold a fluid container 510. In the embodiment shown in FIGS. 6A-6D, each row may include a plurality of compartments 604 each being configured to hold a single sleeve 502. For example, as shown in FIG. 6C, the tray 600 may be configured so that outer surfaces of base portions 512 of the sleeves 502 may engage inner surfaces of the individual compartments 604. In some embodiments, the sizes and shapes of individual compartments may be configured differently to hold differently sized and shaped sleeves and/or carriers. In some embodiments, the rows may not include individual compartments.

In the embodiment shown in FIGS. 6A-6D, tray 600 is configured to hold a plurality of sleeves 502. In other embodiments, an exemplary tray may be configured to hold a plurality of carriers 504. For example, a row or an individual compartment in a row may be configured to hold carrier 504 which may or may not include separable sleeve 502 while in tray 600. A row or an individual compartment in a row may also be configured to hold carrier portion 505 of non-separable carrier 516 shown in FIG. 5D. In some embodiments, an exemplary tray may be configured to hold both sleeves 502 and carriers 504. In the embodiment shown in FIGS. 6A-6D, the tray 600 includes three rows 602 each configured to hold five sleeves 502. In other embodiments, exemplary trays may include any number of rows, each configured to hold any number of sleeves and/or carriers.

The tray may be configured to retain the plurality of carriers 504 and/or sleeves 502 for transporting the tray 600 between loading and unloading of carriers 504 and/or sleeves 502 to and from the tray 600. For example, the rows 602 or individual compartments 604 may be friction fit to retain the plurality of carriers 504 and/or sleeves 502. The tray may be configured to mechanically retain the plurality of carriers 504 and/or sleeves 502, such as for example, by one or more spring loaded devices. The tray may be also be configured to magnetically retain the plurality of carriers 504 and/or sleeves 502. One or more sensors may be used to determine the presence of one or more carriers 504 and/or sleeves 502 in the tray. The one or more sensors may include mechanical sensors (e.g. pressure switches), electrical, magnetic, and/or optical sensors. The tray 600 may be configured to retain the carriers 504 and/or sleeves 502 responsive to the sensed presence of the carriers 504 and/or sleeves 502 in the tray 600.

Figure 7A:
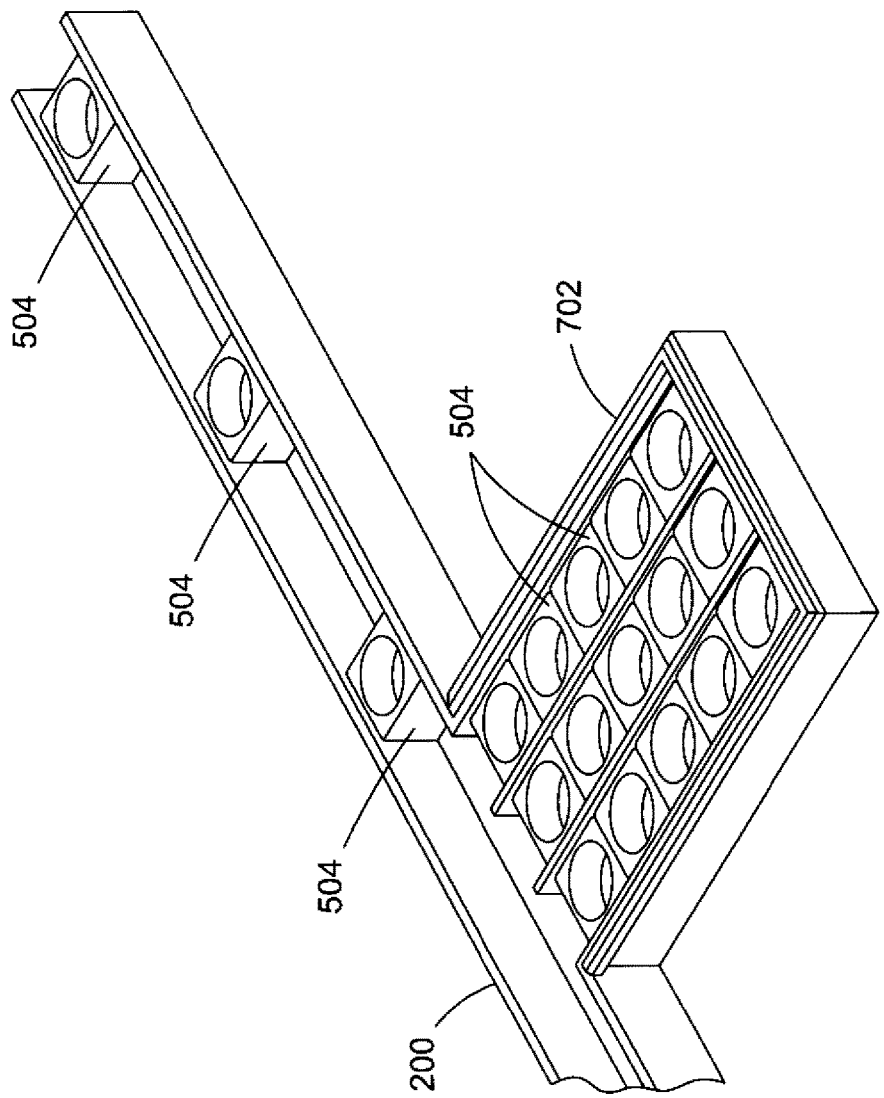
FIG. 7A is a perspective view of a track and loading area having a plurality of carriers that can be used with the embodiments disclosed herein.
Figure 7B:
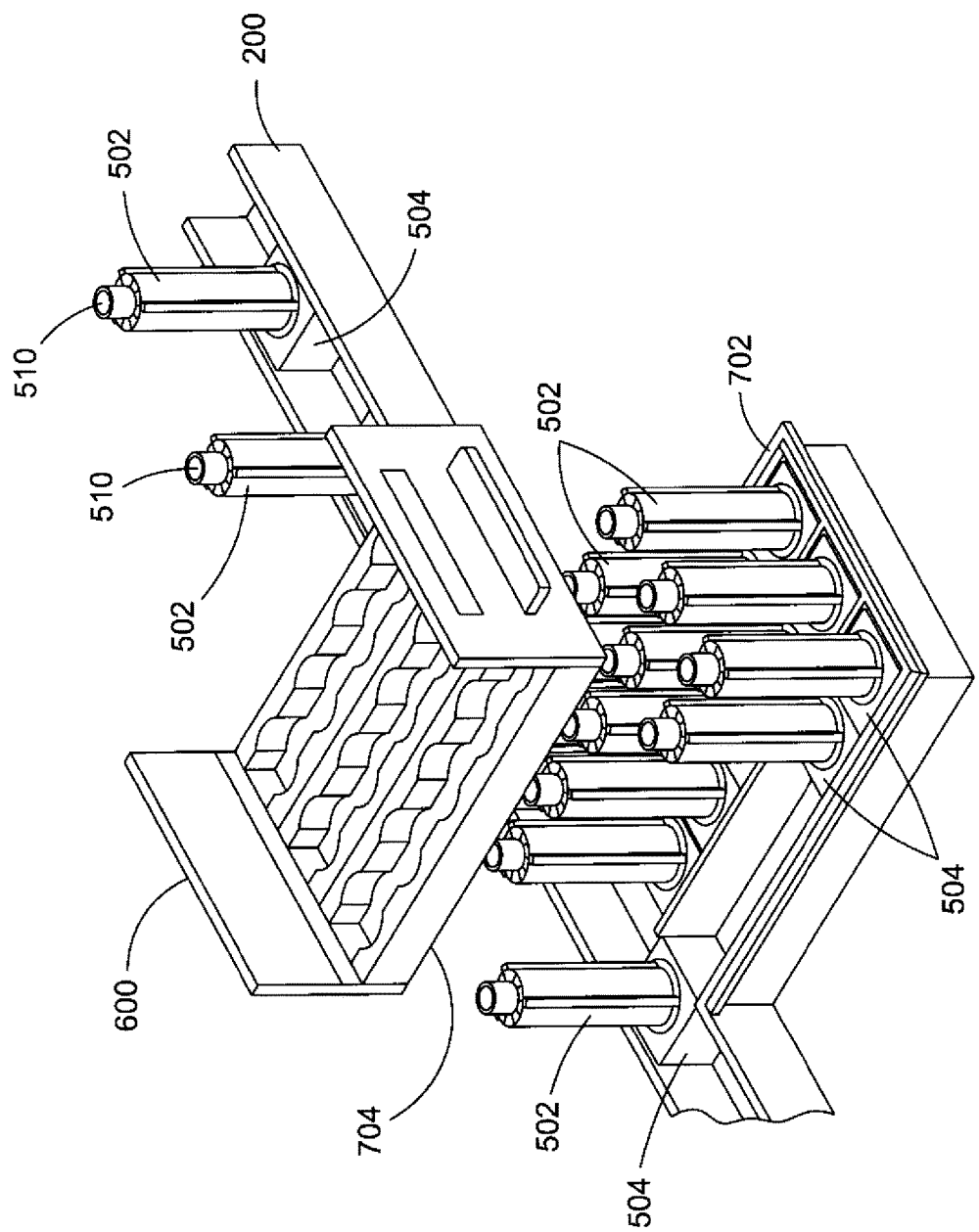
FIG. 7B is a perspective view of an exemplary track, loading/unloading area, a tray, carriers, sleeves and fluid containers illustrating a state of a load-unload operation that can be used with the embodiments disclosed herein.

FIG. 7A and FIG. 7B are perspective views of a track, loading area and tray illustrating different states of load-unload operation. As shown in FIG. 7, an exemplary system may include a loading area 702. As shown in FIG. 7A, loading area may be configured to hold a plurality of carriers 504 and/or carrier portion 505 of non-separable carriers 516. As shown in FIG. 7B, loading area may also be configured to hold a plurality of carriers 504, which may contain a plurality of sleeves 502. In some embodiments, the track 200 may be integral with and include the loading area 702. In other embodiments, the loading area may be separable from the track 702. One or more parameters (e.g., speed of the carrier, direction of the carrier, velocity of the carrier, spacing between carriers, and type of payload) of any one carrier 504, 516, 520 may be different from any other carrier 504, 516, 520 moving along track 200.

The tray 600 may be configured to perform a load-unload operation to the plurality of carriers 504 and/or sleeves 502 through a bottom 704 of the tray 600. The load-unload operation may include an unload function in which the carriers 504 and/or sleeves 502 are unloaded from the tray 600 to the loading area 702. The load-unload operation may also include a load function in which the carriers 504 and/or sleeves 502 are loaded from the loading area 702 into the tray 600. Tray 600 may include one or more handles 606 for an operator to hold while performing a load-unload operation. Handles 606 may also include an actuation device (e.g. a linear actuator) used to release and/or lock carriers 504, 516 and 520 and/or sleeves 502 into individual compartments 604.

An unload function may occur when the plurality of sleeves 502 held by tray 600 shown in FIG. 6C are unloaded through the bottom 704 of tray 600 into carriers 504 in loading area 702 shown in FIG. 7A. After the unload function is performed, the carriers 504 and sleeves 502 may then proceed to enter track 200 from the loading area 702. An operator may then either: (i) wait for a plurality of carriers 504 and/or sleeves 502 to enter the loading area 702 to be loaded into the tray 600 through the bottom 704 of the tray 600, (ii) move to another loading area (not shown) adjacent a track to load a plurality of carriers 504 and/or sleeves 502 from the other loading area into the tray 600 through the bottom 704 of the tray 600; or (iii) move to a remote area (not shown) away from the track to load another plurality of carriers (e.g., by hand or by loading a new pre-arranged set of carriers). Another unload function may then be repeated by unloading the plurality of carriers 504 and/or sleeves 502 (loaded to the tray 600 from the remote area) through the bottom 704 of tray 600 to loading area 702. During an unload function, the tray 600 may also be configured unload each of the carriers 504 and/or sleeves 502 substantially simultaneously from the tray 600. That is, each of the plurality of carriers 504 and/or sleeves 502 in the tray 600 may be automatically or manually released to the loading area at substantially the same time.

A load function may occur when a plurality of sleeves 502 are loaded from loading area 702 through the bottom 704 of tray 600. For example, carriers 504, 516, 520 may enter the loading area 702. The tray 600 may then be placed over each of the plurality of carriers 504, 516, 520 and sleeves 502 in the loading area 702 so that each of the carriers 504, 516, 520 and sleeves 502 are loaded from loading area 702 through the bottom 704 of tray 600. The tray may then be moved by an operator to a remote location to remove the carriers 504, 516, 520 and sleeves 502 from the tray 600. During a load function, the tray 600 may also be configured to load each of the plurality of sleeves 502 and/or each of the plurality of carriers 504, 516, 520 substantially simultaneously to the tray. That is, the tray 600 may be placed over each of the plurality of carriers 504, 516, 520 and/or sleeves 502 in the loading area 702 and each of the plurality of carriers 504, 516, 520 and/or sleeves 502 in the tray 600 may be mechanically or magnetically retained to the loading area at substantially the same time.

Figure 8A:
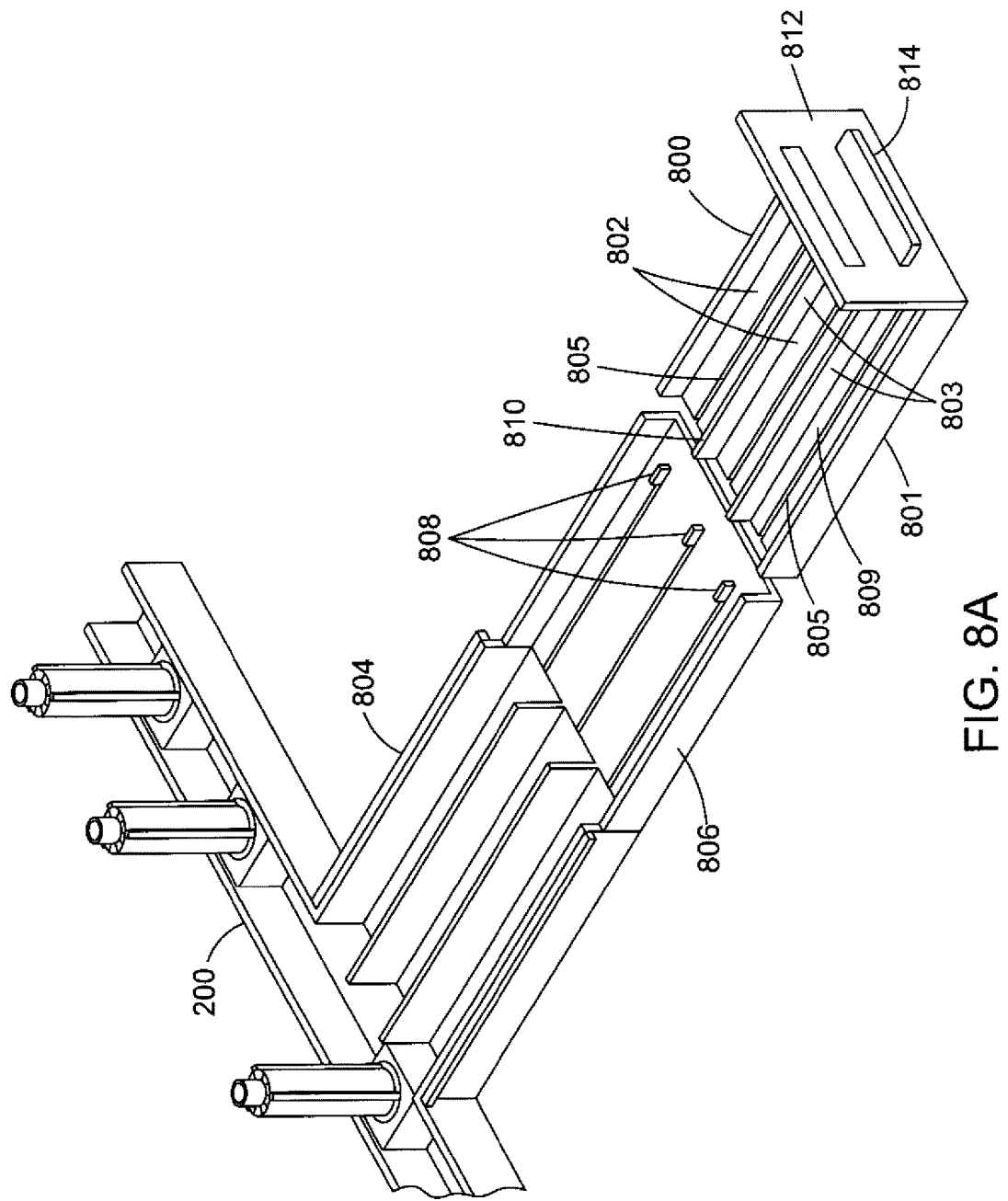
FIG. 8A and FIG. 8B are perspective views of an exemplary edge loading tray, track, loading/unloading area, carriers, sleeves and fluid containers at different states of operation that can be used with the embodiments disclosed herein.
Figure 8B:
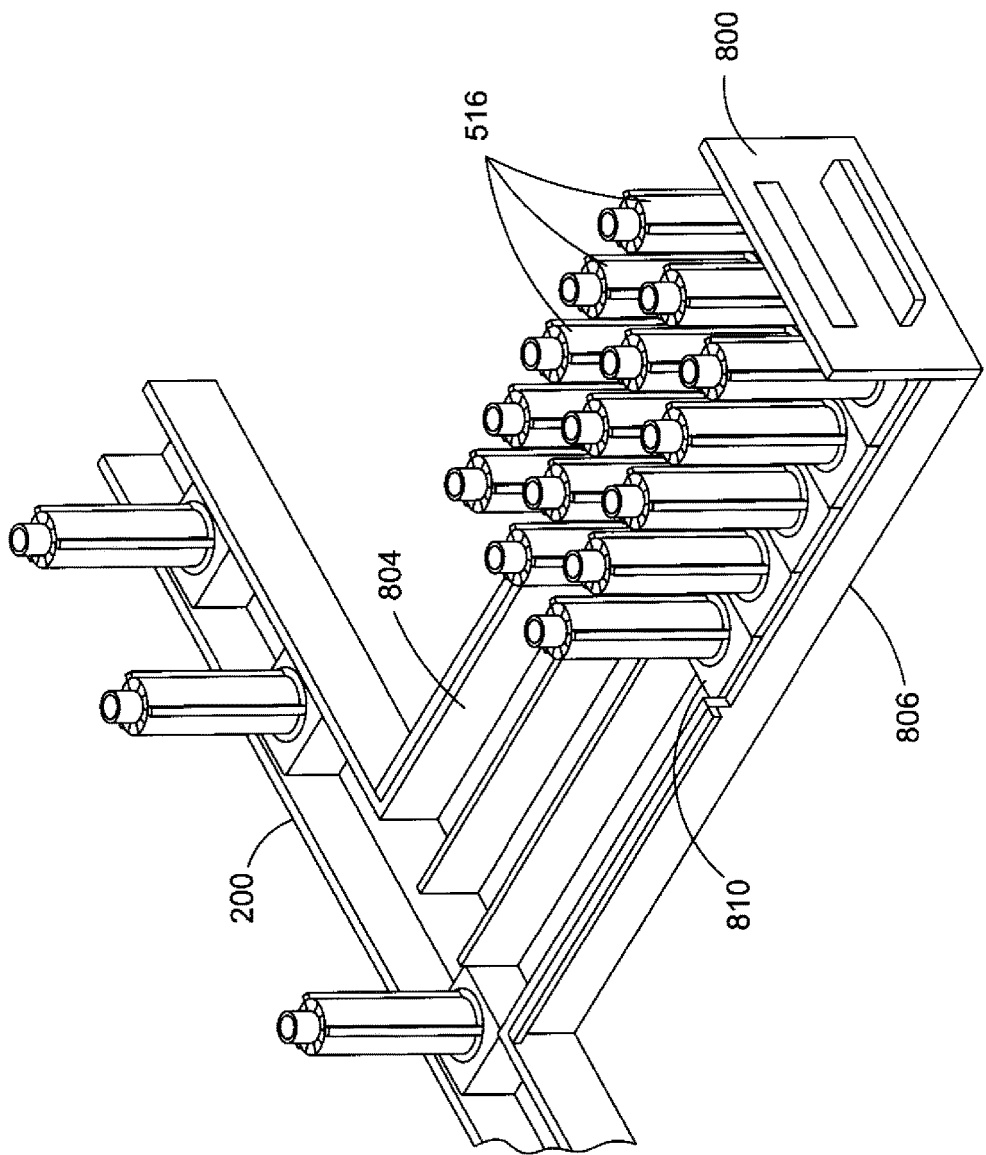

In some embodiments, carriers 504 and/or carriers 516 may be edge (e.g., front edge, back edge, or left and/or right side edge) loaded and edge unloaded to a loading/unloading area 702 or track 200. FIG. 8A and FIG. 8B are perspective views of an exemplary front edge loading tray, tray area, loading area and track at different states of operation. As shown in FIG. 8A, edge loading tray 800 may include a tray body 801 having a plurality of rows 802. As shown in FIG. 8B, rows 802 may be configured for holding the plurality of non-separable carriers 516 (including the sleeve portion 503 and the carrier portion 505 shown in FIG. 5D). The rows 802 may also be configured to hold separable carriers 504 and sleeve 502, multiple slot carriers 520, sleeves 502, (iii) carriers (not shown) configured to directly hold fluid containers 510. Each carrier 504, 516, 520 may be configured to hold the fluid containers 510. For simplification, embodiments described below with regard to edge (e.g. front edge, back edge or left and/or right side edge) loading and/or unloading tray 800 will refer to non-separable carriers 516. Tray 800 may also include tray separator walls 803 configured to separate carriers 516 in each of the rows 802. In some embodiments, the sizes and shapes of edge loading trays and rows may be configured differently to hold different numbers of carriers 516 and differently sized and shaped carriers 516.

The tray 800 may also be configured to perform a load-unload operation to the plurality of carriers 516 through an edge 810 of the tray 800. The load-unload operation may include an unload function in which the carriers 516 are unloaded from the tray 800 to the loading area 804. The load-unload operation may also include a load function in which the carriers 516 are loaded from the loading area 804 into the tray 800. In some embodiments, loading area 804 may be separate from track 200. In some embodiments, track 200 may include loading area 804.

An unload function may occur when the plurality of carriers 516 are unloaded from tray 800 to loading area 804 through edge 810. In the embodiment shown in FIG. 8A and FIG. 8B, each row 802 may include one of a plurality of guides 805 configured to receive a row loading device 808 on tray docking area 806. For example, as shown in FIG. 8B, the tray 800 may be configured to slide onto tray docking area 806 adjacent loading area 804. Tray 800 may also include a rear wall 812 and handle 814 which may be used to assist in sliding tray 800 onto tray docking area 806. When the tray 800 is in a position to have the carriers 516 unloaded from the tray 800, (e.g. at tray docking area 806 as shown in FIG. 8B), each of the row loading devices 808 may move toward loading area 804, thereby moving the carriers 516 to loading area 804 to be unloaded from tray 800 and loaded to onto loading area 200 or directly to the track 200. In some embodiments, a load-unload device may be used to move the sleeves 502 or the carriers 502, 516, 520 between the tray 800 and the track 200. The load-unload device may also be used to move the sleeves 502 or the carriers 502, 516, 520 between the tray 800 and the loading area 804. Load-unload devices may include actuation devices, such as electric, electro-magnetic magnetic and pneumatic actuation devices, and/or mechanisms, such as linear synchronous motors and/or a self-propelled (e.g. motorized) capability built into carrier 504 or carrier portion 505 of non-separable carriers 516. The load-unload device may be used to move one or more row loading devices 808, which in turn, may move the sleeves 502 or the carriers 502, 516, 520 between the tray 800 and the track 200 or loading area 804.

During an unload function, the tray 800 may also be configured to unload rows in parallel. This may provide more options to the system for determining an order of carrier unloading than a system where each carrier must be unloaded in series. For example, the order of unloading carriers may include the following: (Carrier 1) a carrier from a first row may be unloaded; (Carrier 2) a carrier from second row may be unloaded; (Carrier 3) a subsequent carrier from the first row may be unloaded; and (Carrier 4) a carrier from a third row may be unloaded. One reason for unloading these 4 carriers in this order may be to transport these carriers to a single destination, such as a testing station. The next carriers may be unloaded to another destination. Another reason for unloading these four carriers in this order may be to transport carriers holding samples having high priorities, such as STAT samples. In some embodiments, parallel access to the rows of the tray allows substantially simultaneous unloading. For example, the tray 800 may also be configured to unload a carrier 516 from a first row of the plurality of rows 802 substantially simultaneous with carriers 516 from a second and third row of the plurality of rows 802. For example, a row loading device 808 in a first row 802 may move a carrier 516 in the first row 802 onto loading area 200, while a row loading device 808 in a second row 802 substantially simultaneously unloads one carrier 516 in the second row 802 onto loading area 200. Accordingly, a larger amount of carriers may be unloaded to the track quickly.

A load function may occur when a plurality of carriers 516 are loaded from loading area 804 through the edge 810 to the tray 800. For example, carriers 516 may enter the loading area 804 from track 200. Carriers 516 may move directly into tray 800 or may remain in loading area 804 until actuation devices, such as loading devices 808 move the carriers 516 through edge 810 and into tray 800. The tray 800 may then be moved by an operator to a remote location to remove the carriers 516 from the tray 800.

During an unload function, the tray 800 may also be configured to load a first row of the plurality of rows 802 in parallel with a second row of the plurality of rows 802. In some embodiments, the tray 800 may also be configured to load a carrier 516 from a first row of the plurality of rows 802 substantially simultaneous with another carrier from a second row of the plurality of rows 802.

Exemplary row loading devices may also be configured to load and unload carriers from all rows substantially simultaneously. In some embodiments, exemplary row loading devices may alternately load and unload carriers to and from each row. In some embodiments, exemplary row loading devices may load and unload each carrier to and from one row before proceeding to load and unload each carrier to and from another row.

Figure 8D:
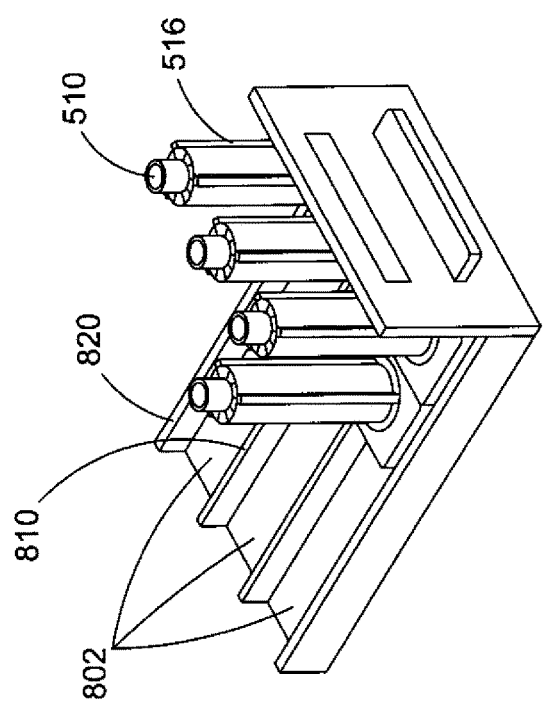
FIG. 8C through FIG. 8E are perspective views of an exemplary edge loading tray, loading/unloading area, track, carriers, sleeves and fluid containers at different states of operation that can be used with the embodiments disclosed herein.
Figure 8C:
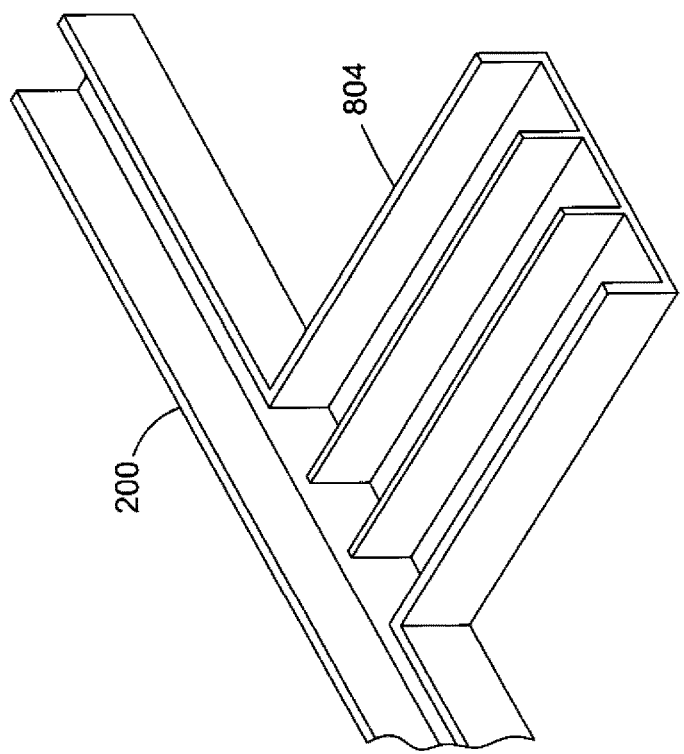
Figure 8E:
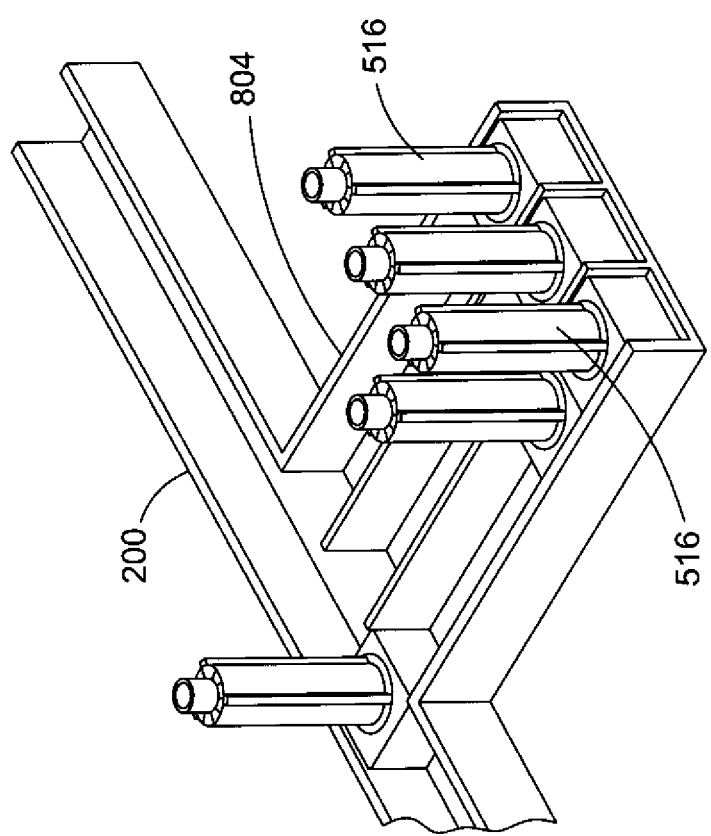

FIGS. 8C-8E are perspective views of an exemplary edge loading tray, loading area and track at different states of operation. In some embodiments, trays, such as tray 820, may not include any carrier moving devices, such as carrier moving devices 808, to load and unload and load the carriers 516 to and from tray 820. For example, the carriers 516 in tray 820 may be loaded and unloaded to and from tray 820 via magnetic motion (described above). In some embodiments, a tray 820, such as tray 820 shown in FIG. 8D, may be placed by an operator adjacent loading area 804, shown in FIG. 8D. Electromagnetic coils and magnets in the carriers, the tray, and/or the loading area operate as linear synchronous motor (LSM) to unload each individual carrier 516 from tray 820 to loading area 804, as shown in FIG. 8E. The electromagnetic coils and magnets may then move each individual carrier 516 between loading and/or unloading area 804 and track 200. In some embodiments self-propelled (e.g., motorized) capability built into carrier 504 or carrier portion 505 of non-separable carriers 516 may be used to move each individual carrier 516 between loading and/or unloading area 804 and track 200.

Figure 9A:
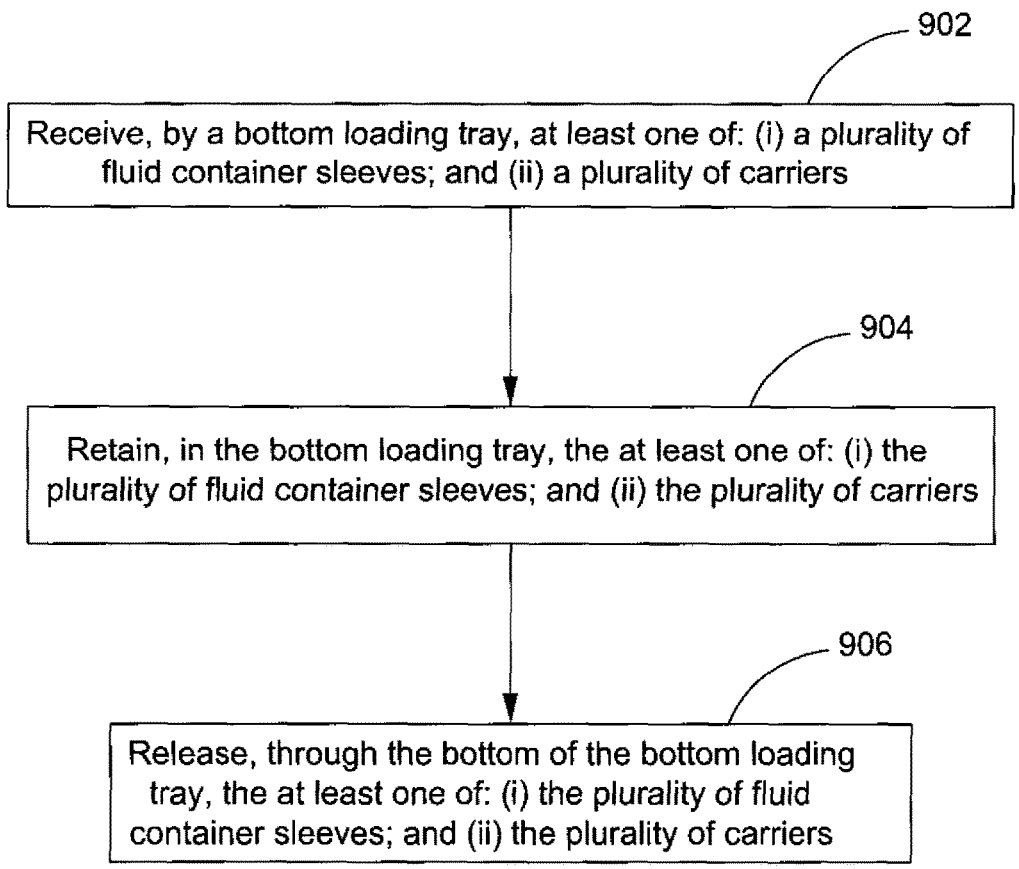
FIG. 9A is a flowchart illustrating an exemplary method for performing a load-unload operation using a bottom loading tray in an in-vitro diagnostics system.

FIG. 9A is a flowchart illustrating an exemplary method for performing a load-unload operation using a bottom loading tray 600 in an in-vitro diagnostics system. As shown at block 902, the method includes receiving by a bottom loading tray 600, at least one of: (i) a plurality of fluid container sleeves 502; and (ii) a plurality of carriers 504, 516. For example, as shown in FIG. 6C, tray 600 may receive fluid container sleeves 502 when outer surfaces of base portions 512 of the sleeves 502 engage inner surfaces of the individual compartments 604 of tray 600. Tray 600 may receive fluid container sleeves 502 when an operator places the tray over sleeves 502, thereby causing each of sleeves 502 to be substantially simultaneously received into tray 600 through the bottom 704 of tray 600. That is, after carriers 504 and sleeves 502 enter loading area 702, as shown in FIG. 7B, tray 600 may receive the fluid container sleeves 502 when an operator places the tray over sleeves 502. Accordingly, carriers 504 may remain in the loading area 702 until new sleeves are placed into the carriers 504 to be loaded onto track 200. In the embodiment shown in FIG. 6C, fluid container sleeves 502 are separable from carriers 504. In other embodiments, tray 600 may receive carriers 516, which include sleeve portion 503 and carrier portion 505. The sleeves 502 and/or carriers 504, 516 may also be individually placed into tray 600 by an operator at a location remote from track 200.

As shown at block 904, the method includes retaining, in the bottom loading tray 600, the least one of (i) the plurality of fluid container sleeves 502; and (ii) the plurality of carriers 504. For example, a mechanical force, such as a spring loaded force, a friction force or a force from an actuation device, may be applied to each of the sleeves 502 to retain the sleeves in the tray 600. In some embodiments, a magnetic force (e.g. using electromagnetic coils and magnets) may be applied to each of the sleeves 502 to retain the sleeves in the tray 600. In some embodiments, the sleeves 502 may be retained responsive to a sensed presence of the sleeves 502 in the tray 600 by one or more sensors.

As shown at block 906, the method includes releasing, through a bottom 704 of the bottom loading tray 600, the at least one of (i) the plurality of fluid container sleeves 502; and (ii) the plurality of carriers 504. For example, when the tray is placed into loading area 702, each of the sleeves 502 may be substantially simultaneously released to the loading area 702 through the bottom of the tray 600 responsive to an operator operating a manual release device. In some embodiments, the plurality of carriers 504 and/or sleeves 502 may be automatically released from the tray 600 in response to a sensed condition. For example, sleeves 502 may be automatically released from tray 600 responsive to determining the tray 600 to be at the loading area 702 by one or more sensors.

Figure 9B:
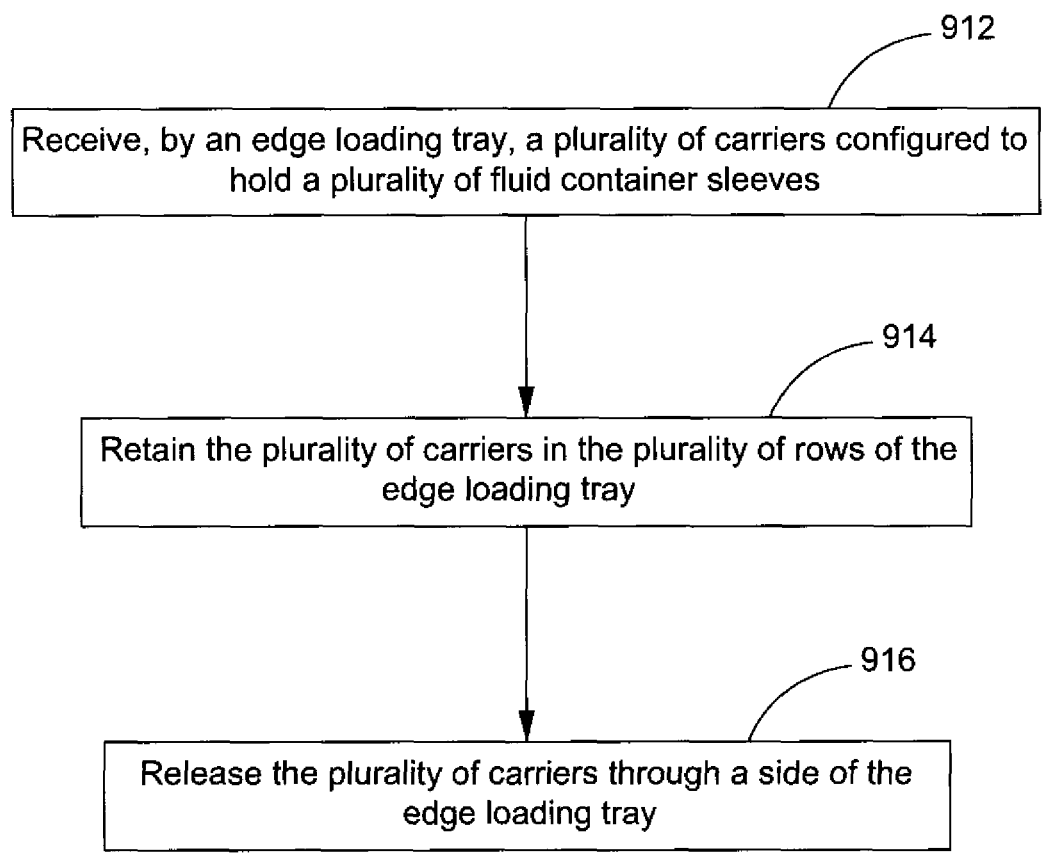
FIG. 9B is a flowchart illustrating an exemplary method for performing a load-unload operation using a edge loading tray in an in-vitro diagnostics system.

FIG. 9B is a flowchart illustrating an exemplary method for performing a load-unload operation using an edge loading tray 800, 820 in an in-vitro diagnostics system. As shown at block 912, the method includes receiving, by an edge loading tray 800, 820, a plurality of carriers 504, 516 configured to hold a plurality of fluid container sleeves 502, 503. For example, as shown in FIG. 8B, a plurality of carriers 516 may be received into a plurality of rows 802 of tray 800. In the embodiment shown in FIG. 8B, tray 800 may receive carriers 516, which include sleeve portion 503 containing a fluid container 510 and carrier portion 505. Accordingly, in this embodiment, carriers 516 may be loaded into tray 800 (e.g. by an operator) at tray docking area 806 or at a location remote from track 200. In another embodiment, tray 800 may receive separable carriers 504 (which do not contain any sleeves or fluid containers) at a location remote from track 200. In this embodiment, the sleeves 502, which are separate from carrier 504 and hold the fluid containers 510, may be loaded into carriers 504 while the tray 800 is at tray docking area 806 or while the carriers 504 are on the track 200. Tray 800 may also receive separable carriers 504 at tray docking area 806 and sleeves 502 may then be placed into the carriers 504 while the carriers 504 are on the track 200.

As shown at block 914, the method includes retaining the plurality of carriers 504, 516 in the plurality of rows 802 of the edge loading tray 800, 820. For example, the carriers may be retained by floor 809 (shown in FIG. 8A). As shown at block 916, the method includes releasing the plurality of carriers 504, 516 through an edge 810 of the edge loading tray 800, 820. For example, in some embodiments, separable carriers 504 may be released into loading area 804 and the sleeves 502 may be loaded into carriers 504 while the carriers 504 are at loading area 804. In other embodiments, carriers 516 (including carrier portion 505 and sleeve portion 503 containing a fluid container) may be released from tray 800 to loading area 804 or to track 200.

Displaying Status Information

A typical operation in an IVD environment begins with receiving a group of fluid samples to be tested. Each tube has a barcode and the tubes are placed into a rack for transporting. An operator then either hand sorts the tubes, or uses an automation device that sorts the tubes for the operator. In the prior art, these tubes would be organized, but an operator carrying a rack of tubes would have little information about, or little ability to determine, the character of each sample. For example, STAT samples may be placed in an input lane of the track system. These samples are deemed important and should be given priority by the operator when handling samples. However, without the ability to tell at a glance which samples are STAT samples, it may be difficult for an operator to handle STAT samples appropriately. Furthermore, not all samples in a rack which has not yet been placed on an automation track may need to go to the same analyzer. This may cause confusion and slow down the process as an operator carries a tray of samples between multiple instruments, modules and/or stations and attempts to select the appropriate samples to be placed into each machine.

Once placed within an analyzer, one or more testing stations interact with each sample. These stations can determine the current properties of the sample, including detecting whether a sample has problems, such as a low volume or precipitates like clots in a whole blood sample. Some samples may need to go to multiple testing stations and have multiple tests performed. In a typical IVD environment, each sample undergoes around half a dozen tests. In some IVD environments, not all tests are performed by the same analyzer or by stations that are accessible be the same automation system. Therefore, in some embodiments, an operator may need to remove a carrier, tube and/or fluid container from an automation system for further processing.

Embodiments of the present invention provide fluid container sleeves, such as fluid container sleeve 502 shown in FIG. 5A, that include one or a plurality of electronically rewritable surface, such as rewritable surface 508 for displaying status information about a sample in a fluid container, such as fluid container fluid container 510 at FIG. 5E. Accordingly, an operator may make visual, dynamic determinations about the particular status of a sample, thereby avoiding the need to remove a carrier 504 or fluid container 510 from an automation system for further processing.

In some embodiments, the sleeve 502 is separable from carrier 504, as shown in FIG. 5C. For example, sleeves 502 may directly engage tray 600, as shown in FIG. 6C, for transport. Sleeves 502 may include an electronically rewritable surface 508. In other embodiments, the carrier 516 may include a carrier portion 505 and a sleeve portion 503. For example, carriers 516 may engage tray 800, as shown in FIG. 8B, for transport. Sleeve portion 503 may include the electronically rewritable surface 508. The display information can continue to be displayed in the tray 600, 800, 820 and, in some embodiments, may continue to be updated wirelessly while in the tray 600, 800, 820. In some embodiments, the sleeves 502 are designed to display status information while within the track system 200 or within an external tray, such as trays 600, 800, 820. Fluid container sleeves 502 may also be used with different types of carriers and fluid containers, such as carrier 250, 504, 516, 1400 and fluid container 255 shown in FIG. 4A and fluid container 510 shown in FIG. 5E. In some embodiments, different types of carriers, fluid containers and sleeves may be used in one automation system.

In some embodiments, a sleeve 502 automatically updates the electronically rewritable display 508 to provide a visual indication of status information regarding one or more fluids in the fluid container. By combining a rewritable surface 508 with an intelligent sleeve 502, the sleeve 502 has means for automatically updating the status and maintaining and displaying that status. For example, as a sleeve 502 moves on a carrier 504 throughout an automation system, it receives information wirelessly from a controller. This information can include routing information as well as status information about the sample being carried. The status information can then be displayed in a rewritable electronic display 508 using the onboard power memory and control available in the sleeve 502.

The rewritable status display 508 can include a top surface of the sleeve 502, as shown in FIG. 5A, FIGS. 5C-5E, FIG. 6C, and FIG. 6D and/or any external surface of any of: (i) sleeve 502, (ii) carrier 504, 516, 520; and (iii) carrier portion 505 of non-separable carriers 516. The display 508 may be an active display, such as an LCD or and bi stable (e.g., E-ink) display. Other embodiments include LEDs, electro florescent displays, AMOLEDs, or any other type of display used in portable or mobile devices. These displays may be volatile, such as LCDs, or nonvolatile, such as bi-stable displays. By using a nonvolatile display, the display can continue to display status information after it has been updated without the need for constantly applying power to the display. An embodiment of the display may be used to identify information relating to fluid containers (e.g. one or more fluids in a fluid container, a person from whom the one or more fluids was taken, an identification number corresponding to the one or more fluids) and/or carriers (e.g. whether carrier is broken) and/or sleeves.

In some embodiments, a bi-stable display is used with a passive sleeve. In these embodiments, an external electric field can be applied to the surface of the sleeve to imprint status information, which will continue to be displayed until rewritten with an electric field. The application of this electric field to the display can be via a planar surface that emits an electric field in a predefined pattern that conveys the status. By placing the display within close proximity to this electric field and the resulting pattern, the display is updated as if it has been electronically stamped. In other embodiments, any display can include pixels or other pattern elements within the display, each served by separate top and/or bottom electrodes. By temporarily applying power to these electrodes, such as by temporary electrical contact, the display can be updated via brief contact and the status information maintained after the contact is broken. In some embodiments, the electronic rewritable display of a sleeve can be updated while in a carrier, but removing the sleeve and loading it into a tray interrupts communication between the automation system and the display. This may allow updated information on the sleeve before the sleeve is loaded into the tray, and subsequent passive display of information when the operator handles the tray. It should therefore be understood that embodiments of the present invention are suitable for use with passive devices as well as the active carriers described herein. In some embodiments the display can be updated via wireless signal.

In some embodiments, a carrier holding a sleeve may include: (i) a processor, such as microcontroller 1401 shown in FIG. 14, configured to update the electronically rewriteable display; and (ii) a wireless transceiver, which may be included in communication system 1415 shown in FIG. 14, configured to receive the status information for display. A processor and wireless transceiver may also be included in the sleeve.

In some embodiments, a sleeve may include an RFID tag having a unique identifier. The RFID tag may be used to determine a chain of custody of the carrier and/or sleeve, past and present locations of the carrier and/or sleeve. In some embodiments, after a bar code on the carrier and/or sleeve is read, only the RFID tag may be needed to identify the carrier and/or sleeve.

In some embodiments, intelligent trays may be used. For example, the electronically rewriteable display may be updated after each carrier and/or sleeve is loaded into the tray. In these embodiments, any subset of the features shown in FIG. 14 may be part of the intelligent tray.

Figure 10A:
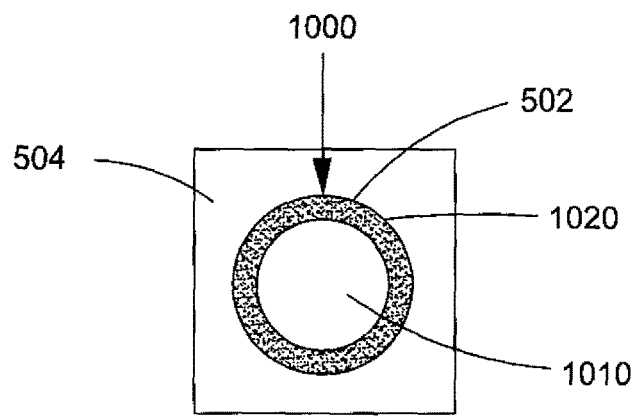
FIG. 10A is a diagrammatic view of an exemplary electronically rewritable surface for displaying status information on a sleeve.
Figure 10B:
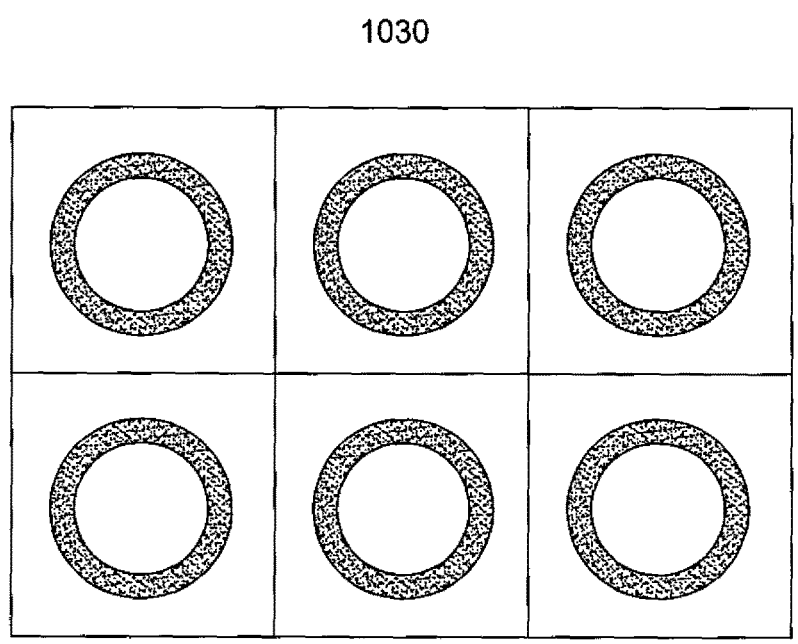
FIG. 10B is a diagrammatic view of multiple exemplary electronically rewritable surfaces for displaying status information on a sleeve.

FIG. 10A shows an exemplary rewritable display 1000. Rewritable display 1000 is shown as the top of the sleeve 502, but other configurations are contemplated. Rewritable display 1000 includes a hollow area 1010 that can be used to accept a sample tube 510 and an electronically rewritable surface 1020. Rewritable surface 1020 can be an LCD panel, or any low powered bi-stable material, which may maintain the image over long period of time, without power, or any other suitable electronic rewritable surface. In some embodiments, the rewritable display can be a portion of the rewritable surface 1020.

As shown in FIG. 6B, multiple carriers can be placed in an array 1030, such as when placed in a tray for easy handling by an operator. For example, after samples are sorted by a sorter or an operator, carriers containing samples can be placed in array 1030 and information about the status of each sample in the array 1030 can be displayed in the surfaces of the rewritable displays of each carrier.

Information can be conveyed via the rewritable surface in several ways, depending on the capabilities of the display surface used. First, color can be used to convey status information. For example, green can show that a sample has completed processing or has successfully passed a quality test. Yellow may show that a sample is still awaiting further testing. Red may show that the sample has an error, such as that foreign bodies have been detected, that the sample is too low on volume to be further tested, etc. STAT samples can also include their own color, such as blue, so that they are readily identifiable next to normal priority samples.

Second, a pattern can be used to convey information. For example, shapes such as diamonds, triangles, squares, circles, logos, textures, or other symbols that are easily differentiated can be displayed on the surface to indicate information about status to an operator. The pattern displayed can also be time varying—a blinking pattern or color can indicate importance of the sample, such as an error. Third, text can be displayed on the surface of the carrier to indicate specific information to an operator, such as the next destination, or the identity of a sample. This text can be helpful in identifying specific samples that an operator is looking for, without the need to scan each barcode since the text is human readable.

FIG. 11 shows some exemplary embodiments of visual patterns that can be used to display status information in a rewritable surface of the carrier. Surface 1141 shows a blank display, which indicates that a tube is not present or identified. Surface 1142 includes a main area whose color or shading indicates the presence of a tube, while a smaller region of the surface is blank, indicating the priority (e.g., normal) of the tube. Patterns 1144 show exemplary alternative displays for indicating a sample is waiting. These patterns can include a solid shaded or colored surface or text indicating that a sample is waiting. Shading can be accomplished using a digital gray scale value that can be accomplished by partially turning on/off portions of the display (e.g., pixels or regions) or by pulse width modulation of these portions.

Surface 1146 includes a main area whose color or shading indicates the presence of a tube, while a smaller region of the surface is solid or colored red, indicating the priority (e.g., STAT) of the tube. Surface 1147 shows an alternate embodiment for displaying a STAT sample, including the use of a text field that identifies the sample. Surface 1148 shows an example of an embodiment of the surface for indicating that a sample is waiting to be transferred to a specific analyzer or testing station. This includes a text field for displaying the identity of the sample and another text field for identifying the intended destination of the sample, or instructions for the operator to follow. By using instructions, an operator can easily determine what to do with a sample with minimal or no training.

Surface 1149 shows an exemplary embodiment for displaying an error. A main area displays an error color (e.g., red) or pattern (e.g., striped, blinking, etc.), while a first text field displays the identity of the sample and a second text field displays the nature of the error, such as indicating the sample is low on volume (e.g., "short sample").

Embodiments can include a text field that includes the identity of the sample. This identity can be the unique identifier in the barcode of the sample or any other indicator of identity, including an ID that is only used in the IVD environment or sample type, patient name, or a record identifier.

Figure 12:
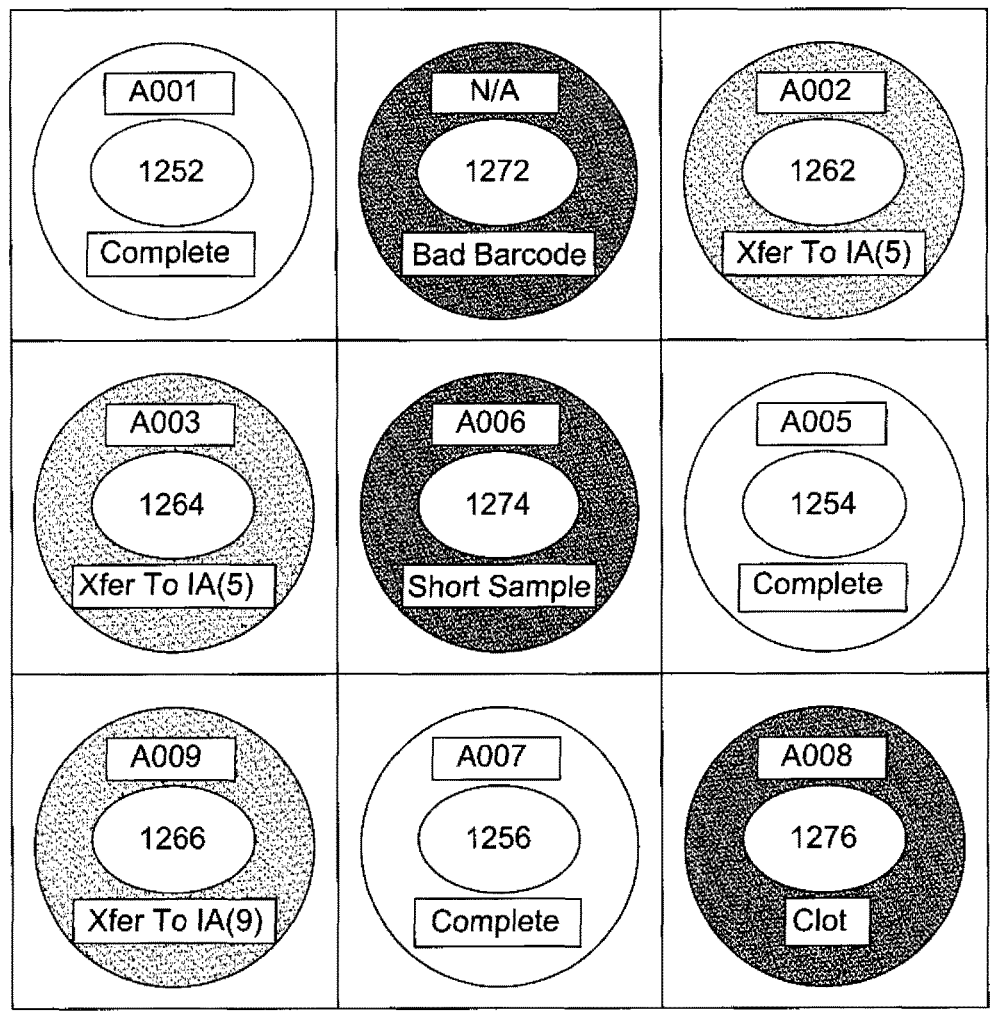
FIG. 12 is a diagrammatic view of multiple exemplary states of electronically rewritable surfaces for displaying status information about a samples arranged in an array.

FIG. 12 shows an exemplary array of carriers that display the status of multiple samples. In this example, carriers 1252, 1254, 1256 indicate completed samples. A main area includes a first color or pattern, such as green or white that indicates the completed state of the sample. A first text field indicates the identity of each sample, while a second text field indicates the completed status of the sample. Carriers 1262, 1264, and 1266 indicate that testing is pending on those samples. A main area includes a first color or pattern, such as gray or yellow to indicate this pending status. A first text field indicates the identity of each sample, while a second text field indicates instructions to the operator or the next step that an automation system will execute to complete the testing on the sample. Carriers 1272, 1274, and 1276 indicate the presence of an erroneous sample. A main area includes a first color pattern, such as red or black that indicates the error state of the sample. Meanwhile, a first text field indicates the identity of the sample (if known), while a second text field indicates the specific nature of the error. For example, carrier 1272 indicates that there is a barcode error with a sample so that its identity cannot be ascertained. Carrier 1274 indicates that the volume of sample is insufficient for further testing. Carrier 1276 indicates the presence of a clot the sample.

Figure 13:
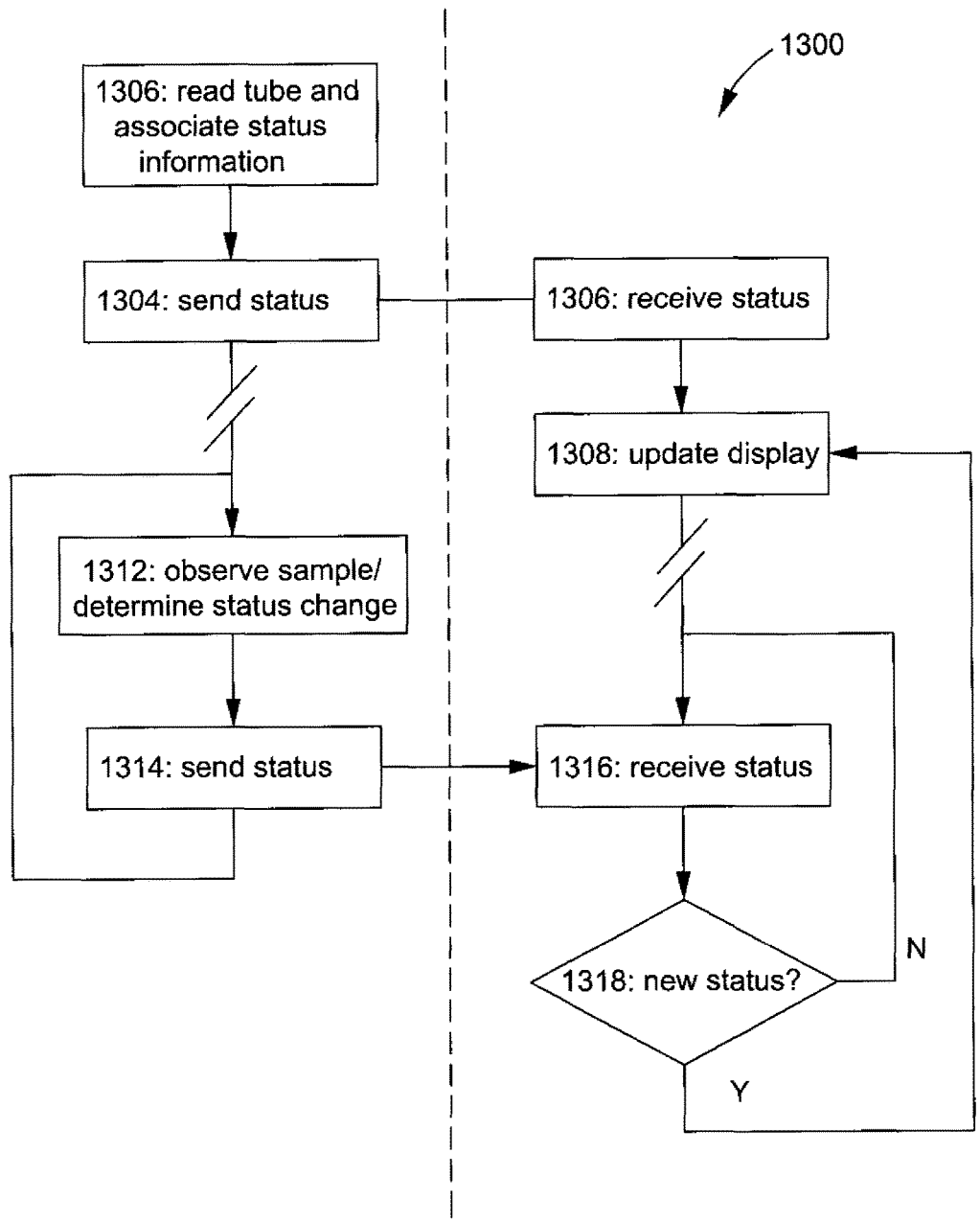
FIG. 13 is a flowchart showing an exemplary operation of an embodiment of an electronically rewriteable status display.

FIG. 13 shows a flowchart of the basic operation 1300 of the rewritable display. At step 1302, the system reads information about the tube and associates it with the carrier. This can include, for example, scanning of a barcode either automatically or by hand. It can also include using onboard sensors of the carrier to detect the presence of the tube. In some embodiments, step 1302 is performed at a system level and the status information of the tube is maintained by a central processor in an automation system. At step 1304, the status is communicated to the carrier. In some embodiments, this communication is via wireless communication.

At step 1306, the carrier receives status information from the central processor and stores this information in onboard memory. At step 1308, the carrier updates the rewritable display panel to indicate the current status. As the carrier moves the sample throughout the automation system, and testing stations interact with the sample, the status can change. At step 1312, the automation system observes the sample and determines if the status has changed. This can occur, for example, when a sample pipette interacts with the sample to detect the volume and quality of the sample. This information can be used to determine a status (e.g., an error) of the sample. Furthermore, once a testing station completes a test on the sample, the status of the sample (such as next test, pending/complete, etc.) will change. At step 1314, the updated status is sent to the carrier wirelessly.

At step 1316, the carrier receives the new status from the automation system via the wireless transceiver. At step 1318, the carrier determines if the status is now different than that being displayed. If not, the carrier continues to wait for further updates to the status of the sample. If the status has changed and the display should be updated, the carrier then updates the display at step 1308.

In some embodiments, an operator receives a rack of tubes for testing. These tubes are not yet placed into carriers. An operator will scan the barcodes of each so that the automation system knows the identity and other information, such as the scheduled tests for the sample. A central processor for the automation system will then assign the tube to a specific carrier. The central processor can then communicate this relationship to that carrier, causing the assigned carrier to blink or light up. This allows the operator to determine which carrier the tube has been assigned to, and place the tube in the proper carrier.

In some embodiments, after a tube has been scanned by an operator, the central processor will begin polling carriers in the area and identify which carriers receive a new tube within a short period of time after the tube has been scanned. In this way, the central scheduler can automatically identify the carrier into which the operator has placed the tube. Once the identity of the carrier is known, the central processor can communicate status information about the tube/sample, such as identity, to the appropriate carrier. This can be used to ensure reliable chain of custody for samples.

The status display can also be used, in some embodiments, to indicate whether a sample in a carrier meets certain operator-defined criteria. For example, an operator may want to determine which samples are associated with a certain patient. The operator can submit a query to the central controller that communicates status information to the carriers. The controller can determine which samples match the query by comparing the query to a database of status information of the samples in the IVD environment. This can be maintained by the central controller. In response to the query, the central controller can then update the status information of the responsive carriers such that they can temporarily display their inclusion in a responsive group of carriers. For example, the central controller can send instructions wirelessly to all carriers of samples of the requested patient to cause their displays to blink, so that an operator can tell at a glance which samples are responsive to the query.

Smart Carriers

Whereas some embodiments may utilize passive pucks or trays (e.g., the puck is a simple plastic or rubber brick that lacks active or autonomous systems, power, onboard processing, or control) to reduce cost and complexity, in some embodiments, the added complexity and cost necessary to integrate intelligence and autonomy into individual carriers (which can include smart pucks or trays in some embodiments) can provide certain benefits. Accordingly, embodiments of the present invention can utilize intelligent carriers to enable certain improvements over passive pucks on the friction-based tracks. For example, one disadvantage of prior art track systems is that at each decision point the decision for directing a puck is made by the track by rotating the puck and reading a barcode optically. Rotating and optical reading is a relatively slow process. Furthermore, this process can be redundant because the system has a prior knowledge of the identification of the sample tube when the sample tube is placed into the puck by an operator. Embodiments of the present invention can include carriers that have means to identify the contents of the sample tube (and optionally communicate this information to the automation system) without requiring the carrier to be stopped, rotated, and read optically.

For example, a carrier can include an onboard optical reader to automatically read a barcode of a payload. The results of the scan can then be stored in the memory of a carrier if the carrier has onboard processing capability. Alternatively, an outside source, such as a hand barcode reader operated by an operator at the time of placing the sample into the carrier, can communicate the barcode information of the payload to the carrier via RF signal or other known means, such as communication protocol using temporary electrical contact or optical communication. In some embodiments, the association of the carrier with the payload can be stored external to the carrier and the identity of the carrier can be conveyed by the carrier to the system by RF, optical, or near-field communication, allowing the system to assist in routing or tracking the carrier and the payload. Routing decisions can then be made by the carrier or by identifying the carrier, rather than reading a unique barcode of a payload.

By moving processing capability and/or sensor capability onto each individual carrier, the carriers can participate actively and intelligently in their own routing through the track system. For example, if individual carriers can move independently of one another either by autonomous motive capabilities or by communication with the track, certain performance advantages can be realized.

By allowing carriers to move independently, carriers can move around the track faster. One key limitation on the motion of a carrier is that it should not spill an open-tube sample. The limiting factor is generally not the velocity of the carrier in a straight line, but the acceleration and jerk experienced by the carrier (while speeding up, slowing down, or turning), which may cause splashing. For prior art friction-based track systems, the velocity of the track is typically limited to prevent acceleration and jerk experienced by pucks from exceeding threshold amounts because the entire track moves. However, by using a track system with independently operating sections that can respond to individual carriers, or individual carriers that have independent motive capability, the acceleration of any given carrier can be tailored to limit acceleration/deceleration and jerk, while allowing the average velocity to be greater than that of traditional tracks. By not limiting the top speed of a carrier, the carrier can continue to accelerate on each track section as appropriate, resulting in a substantially higher average speed around the track. This can assist the carrier in traversing the entire track system in less than one machine cycle of the analyzer. These machine cycles can be, for instance 20 or 40 seconds.

Similarly, an autonomous carrier can know its own identity and that of its payload. This allows the carrier to actively participate or assist in the routing decision process at individual decision points. For example, upon reaching a decision point (e.g., switch, intersection, junction, fork, etc.), a carrier can communicate its identity and/or the identity of its payload to the track or any switching mechanism (or its intended route that the carrier has determined based on the payload identity), via RF or near-field communication. In this scenario, the carrier does not need to be stopped at a decision point for a barcode scan. Instead, the carrier can keep going, possibly without even slowing down, and the carrier can be routed in real time. Furthermore, if the carrier knows where it is going or communicates its identity to the track (such that the track knows where the carrier is going) before the carrier physically reaches a decision point, the carrier can be made to decelerate prior to a decision point if the carrier will be turning. On the other hand, if the carrier does not need to turn at the decision point, the carrier can continue at a higher velocity because the sample carried by the carrier will not undergo cornering forces if the carrier is not turning at the decision point or a curved section of the track.

An autonomous carrier can also include onboard processing and sensor capabilities. This can allow a carrier to determine where it is on the track and where it needs to go, rather than being directed by the track (although in some embodiments, a central controller sends routing instructions to the carrier to be carried out). For example, position encoding or markers in the track can be read by a carrier to determine the carrier's location. Absolute position information can be encoded on a track surface to provide reference points to a carrier as it traverses the track. This position encoding can take many forms. The track may be encoded with optical markers that indicate the current section of the track (e.g., like virtual highway signs), or may further include optical encoding of the specific absolute location within that section of track (e.g., like virtual mile markers). Position information can also be encoded with markings between absolute position marks. These can provide synchronization information to assist a carrier in reckoning its current trajectory. The optical encoding scheme may take on any appropriate form known to one skilled in the art. These marks used by the encoding scheme may include binary position encoding, like that found in a rotary encoder, optical landmarks, such as LEDs placed in the track at certain positions, barcodes, QR codes, data matrices, reflective landmarks, or the like. General position information can also be conveyed to the carrier via RF/wireless means. For example, RFID markers in the track can provide near field communication to the carrier to alert the carrier that it has entered a given part of the track. In some embodiments, local transmitters around or near the track can provide GPS-like positioning information to enable the carrier to determine its location. Alternatively, sensors in the track, such as Hall effect sensors or cameras, can determine the position of individual carriers and relay this information to the carrier.

Similarly, the carrier can have sensors that indicate relative motion, which provide data that can be accumulated to determine a position between absolute position marks. For example, the carrier may have gyroscopes, accelerometers, or optical sensors that observe speckle patterns as the carrier moves to determine velocity or acceleration, which can be used to extrapolate a relative position. In some embodiments, components include a light source and an image sensor that can be used to observe the relative motion of the track surface with respect to the carrier to determine a real-time trajectory estimate. For example, after reckoning its position with an absolute position mark, the carrier can observe successive images of a track surface and compare these images to determine the direction and magnitude of motion. This can be used to determine real-time position, velocity, acceleration, and jerk, or estimates thereof. In addition, synchronous marks, such as marks placed at regular intervals in the track, can be used to reckon the carrier's position between absolute position marks and can correct errors that may have accumulated in the real-time trajectory information determined from observation of the relative motion of the surface of the track. This can allow a lower sampling frequency or less precise components in the position decoding imaging sensor.

Because a carrier can know where it is and its motion relative to the track, a carrier can essentially drive itself, provided it knows its destination. The routing of the carrier can be provided in many different ways in various embodiments. In some embodiments, when a carrier is loaded with the sample, the system can tell the carrier the destination analyzer station. This information can be as simple as the identification of the destination station in embodiments where the carrier has autonomous routing capability. This information can also be detailed information such as a routing list that identifies the specific path of the individual track sections and decision points that a carrier will traverse. Routing information can be conveyed to the carrier via any communication method described herein, such as RF communication, near-field/inductive communication, electrical contact communication, or optical communication.

In an exemplary embodiment, when an operator scans the barcode of the sample tube and places it in a carrier, the system determines the identity of the carrier and matches it with the identity of the sample. The system then locates the record for the sample to determine which tests the sample must undergo in the analyzer. A scheduler then allocates testing resources to the sample, including choosing which tests will be done by individual testing stations and when the sample should arrive at each testing station for analysis. The system can then communicate this schedule (or part of the schedule) to the carrier to inform the carrier of where it needs to go, and optionally when it needs to go and/or when it needs to arrive.

Once the carrier is placed onto the track system, the routing capabilities and location acquisition systems of the carrier enable the carrier to determine where it is on the track and where it needs to go on the track. As the carrier traverses the track, the carrier reaches individual decision points and can be directed along the main track or along sub-paths as appropriate. Because each carrier operates independently from one another, a carrier can do this quite quickly without necessarily stopping at each decision point and without waiting for other carriers in a queue. Because these carriers move quickly, there is less traffic on the main sections of the track, which reduces the risk of collision or traffic jams at decision points or corners in the track (e.g., sections where carriers might slow down to avoid excessive forces on the sample).

Motive force can be provided to the carriers in many ways. In some embodiments, the track actively participates in providing individualized motive force to each carrier. In some embodiments, motive force is provided by electromagnetic coils in the track that propel one or more magnets in the carrier. An exemplary system for providing this motive force is the track system provided by MagneMotion, Inc., which can generally be understood by the description of the linear synchronous motors (LSMs) found in US Published Patent Application 2010/0236445, assigned to MagneMotion, Inc. These traditional systems utilizing this magnetic motion system have included passive carriers that lack the integrated intelligence of the carriers described herein, and all routing and decisions are made by a central controller with no need for active carriers that participate in the routing and identification process.

In embodiments that utilize magnetic motion, the electromagnetic coils and the magnets operate as an LSM to propel each individual carrier in the direction chosen with precise control of velocity, acceleration, and jerk. Where each coil on the track (or a local set of coils) can be operated independently, this allows highly localized motive force to individual carriers such that individual carriers can move with their own individually tailored accelerations and velocities. Coils local to a carrier at any given moment can be activated to provide precise control of the direction, velocity, acceleration, and jerk of an individual carrier that passes in the vicinity of the coils.

In some embodiments, a track may be comprised of many individually articulable rollers that act as a locally customizable friction track. Because individual micro-sections of the track can be managed independently, rollers immediately around a carrier may be controlled to provide individualized velocity, acceleration, and jerk. In some embodiments, other active track configurations can be used that provide localized individual motive force to each carrier.

In some embodiments, the track may be largely passive, providing a floor, walls, rails, or any other appropriate limitations on the motion of a carrier to guide the carrier along a single dimension. In these embodiments, the motive force is provided by the carrier itself. In some embodiments, each individual carrier has one or more onboard motors that drive wheels to provide self-propelled friction-based motive force between the track and the carrier. Unlike traditional friction tracks, where the track is a conveyor, carriers with driven wheels can traverse the track independently and accelerate/decelerate individually. This allows each carrier to control its velocity, acceleration, and jerk at any given moment to control the forces exerted on its payload, as well as traverse the track along individually tailored routes. In some embodiments, permanent magnets may be provided in the track and electromagnets in the carrier may be operated to propel the carrier forward, thereby acting as an LSM with the carrier providing the driving magnetic force. Other passive track configurations are also contemplated, such as a fluid track that allows carriers to float and move autonomously via water jets or the like, a low friction track that allows carriers to float on pockets of air provided by the track, (e.g., acting like a localized air hockey table), or any other configuration that allows individual carriers to experience individualized motive forces as they traverse the track.

Figure 14:
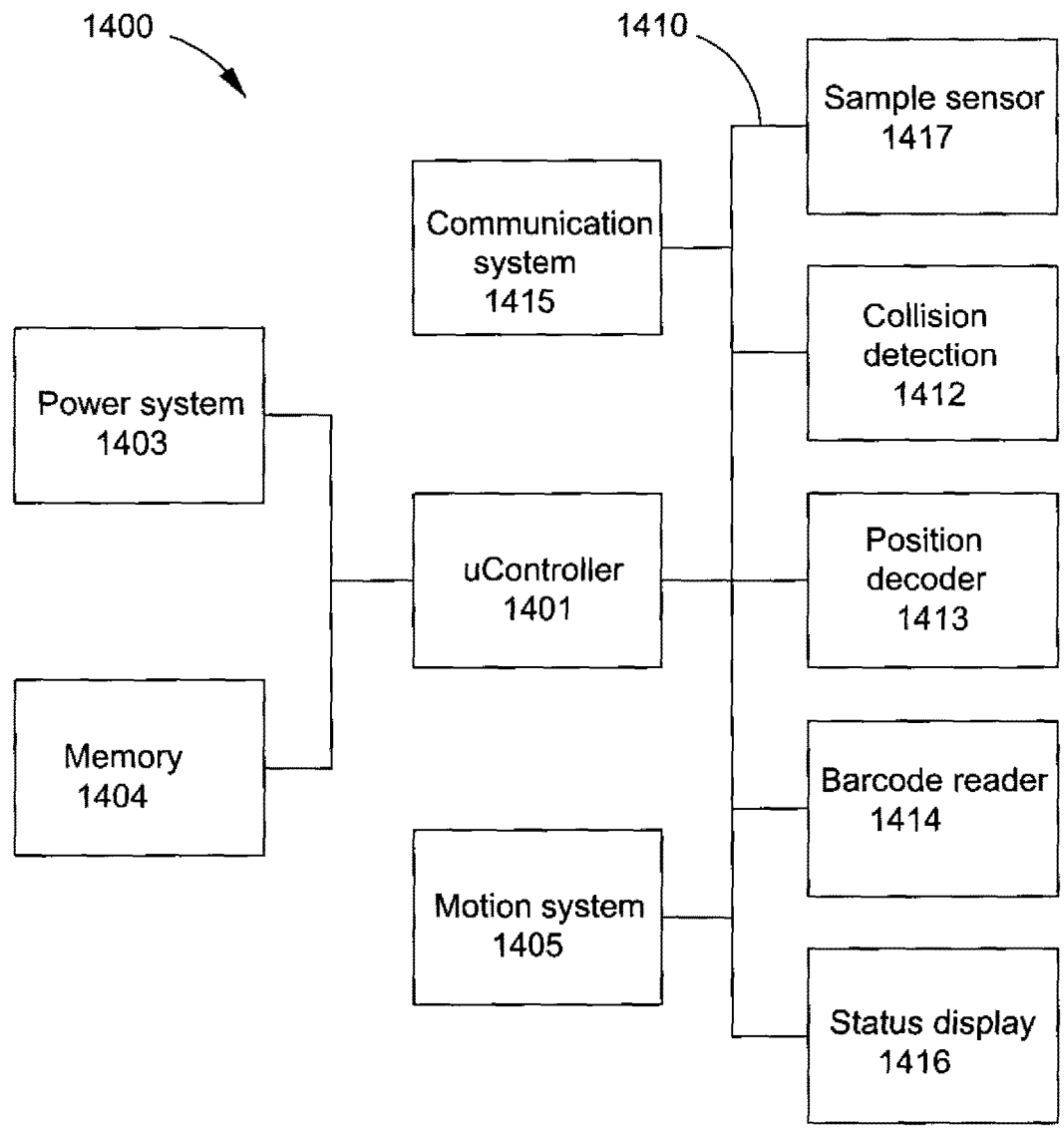
FIG. 14 is a system block diagram of the control systems including onboard active carriers that can be used with certain embodiments disclosed herein.

In some embodiments, an automation system may include intelligent autonomous carriers 1400. FIG. 14 shows a top level system diagram of the control systems and sensors for an intelligent autonomous carrier 1400. Carrier 1400 is controlled by a microcontroller 1401 that includes efficient processing power to handle navigation, maintenance, motion, and sensor activities needed to operate the carrier. Because the carrier is active and includes onboard electronics, unlike prior art passive carriers, the carrier includes an onboard power station. The details of this station vary in different embodiments of the present invention. In some embodiments, power system 1403 comprises a battery that may be charged as the carrier operates, while in other embodiments, the battery is replaceable or can be manually charged when the carrier is not operating. Power system 1403 can include the necessary charging electronics to maintain a battery. In other embodiments, the power system 1403 comprises a capacitor that may be charged by inductive or electrical contact mechanisms to obtain electrical potential from the track itself, in much the same way a subway car or model train might receive power.

Microcontroller 1401 communicates with system memory 1404. System memory 1404 may include data and instruction memory. Instruction memory in memory 1404 includes sufficient programs, applications, or instructions to operate the carrier. This may include navigation procedures as well as sensor handling applications. Data memory in memory 1404 can include data about the current position, speed, acceleration, payload contents, navigational plan, identity of the carrier or payload, or other status information. By including onboard memory in carrier 1400, the carrier can keep track its current status and uses information to intelligently route around the track or convey status information to the track or other carriers.

Microcontroller 1401 is responsible for operating the motion system 1405, sensors 1412, 1413, and 1414, and communication system 1415. These peripherals can be operated by the microcontroller 1401 via a bus 1410. Bus 1410 can be any standard bus, such as a CAN bus, that is capable of communicating with the plurality of peripherals, or can include individual signal paths to individual peripherals. Peripherals can utilize their own power sources or the common power system 1403.

Motion system 1405 can include the control logic necessary for operating any of the motion systems described herein. For example, motion system 1405 can include motor controllers in embodiments that use driven wheels. In other embodiments, motion system 1405 can include the necessary logic to communicate with any active track systems necessary to provide a motive force to the carrier 1400. In these embodiments, motion system 1405 may be a software component executed by microcontroller 1401 and utilizing communication system 1415 to communicate with the track. Devices such as motors, actuators, electromagnets, and the like, that are controlled by motion system 1405 can be powered by power system 1403 in embodiments where these devices are onboard the carrier. External power sources can also provide power in some embodiments, such as embodiments where an LSM provides motive force by energizing coils in the track. In some embodiments, motion system 1405 controls devices on or off the carrier to provide motive force. In some embodiments, the motion system 1405 works with other controllers, such as controllers in the track, to coordinate motive forces, such as by requesting nearby coils in the track be energized or requesting the movement of local rollers. In these embodiments, motion system 1405 can work together with communication system 1415 to move the carrier.

Carrier 1400 can include one or more sensors. In some embodiments, carrier 1400 includes a collision detection system 1412. Collision detection system 1412 can include sensors at the front or back of a carrier for determining if it is getting close to another carrier. Exemplary collision detection sensors can include IR range-finding, magnetic sensors, microwave sensors, or optical detectors. Whereas many prior art pucks are round, carrier 1400 may be directional, having a front portion and a rear portion. By having a directional geometry, carrier 1400 can include a front collision detector and a rear collision detector.

In some embodiments, collision detection information can include information received via the communication system 1415. For example, in some embodiments, the central controller for the track can observe the location and speed of carriers on the track and evaluate collision conditions and send updated directions to a carrier to prevent a collision. In some embodiments, nearby carriers can communicate their positions in a peer-to-peer manner. This allows carriers to individually assess the risk of collision based on real-time position information received from other carriers. It will be understood that in embodiments where the carrier receives trajectory information about other carriers, or decisions are made with the help of a centralized controller that has access to trajectory information of nearby carriers, the carriers need not be directional, and can include sensors or receivers that do not depend on a given orientation of a carrier.

Carrier 1400 can also include a position decoder 1413. This sensor can extrapolate the carrier's position as described herein. For example, position decoder 1413 can include a camera or other optical means to identify landmarks in the track, or observe optical encoding in the track. In some embodiments, position decoder 1413 can also include inertial sensors, magnetic sensors, or other sensors sufficient to determine a carrier's current position, direction, velocity, acceleration, and/or jerk.

Carrier 1400 can optionally include a barcode reader 1414. If equipped with the barcode reader 1414, carrier 1400 can observe the barcode of its payload at the time the samples are loaded onto the carrier or at any time thereafter. This prevents the need for a carrier to stop at individual decision points to have the system read the barcode of a sample tube. By reading and storing the identity of the sample tube, or conveying this information to the overall system, a carrier may more efficiently traverse the track system because routing decisions can be made in advance of reaching a decision point. Alternatively, where a system knows the identity of the sample when it is placed onto the carrier, the system can include an external barcode reader and can convey the identity of the payload to the carrier for storage and memory 1404 via communication system 1415.

Communication system 1415 can comprise any mechanisms sufficient to allow the carrier to communicate with the overall automation system. For example, this can include an XBee communication system for wireless communication using an off-the-shelf communication protocol, such as 802.15.4, any appropriate version of 802.11, or any standard or proprietary wireless protocol. Communication system 1415 can include a transceiver and antenna and logic for operating an RF medication protocol. In some embodiments, communication system 1415 can also include near-field communication, optical communication or electrical contact components. Information conveyed via the communications system to/from carrier 1400 is described throughout this application.

In some embodiments, the carrier can also include a status display module 1416. The status display module 1416 can include a controller and rewritable electronic display, such as an LCD panel or E-ink display. In some embodiments, the controller is treated as an addressable portion of memory, such that the microcontroller 1401 can easily update the status display 1416.

In some embodiments, the carrier also includes sample sensor 1417. This sensor can be used to indicate the presence or absence of a sample tube in the carrier's tube bracket. In some embodiments, this is a momentary mechanical switch that is depressed by the presence of a tube and not depressed when a tube is absent. This information can be used to determine the status of a tube, which can assist in the display status information by status display module 1416.

It should be understood that in embodiments that utilize separable sleeves, any subset of the system components shown in FIG. 14 may be replicated or moved into the sleeve. Accordingly, in some embodiments, FIG. 14 can depict a system where some components are in a carrier body, while other components are in the sleeve. The boundary between the sleeve components and the carrier components can be any suitable boundary, including placing a subset of the electronic devices that communicate with bus 1410 in the sleeve, while the remaining devices are part of the main body of a carrier that holds the sleeve.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. An automation system for use with in-vitro diagnostics comprising:
   a track configured to provide one or more paths;
   a plurality of fluid containers comprising tubes configured to hold a patient sample;
   a plurality of sleeves, each sleeve comprising a hold configured to engage one of the plurality of fluid containers and a base portion configured to engage a corresponding receptacle of a carrier for transport;
   a plurality of carriers configured to travel along the track, each carrier separable from each sleeve and configured to hold one of the plurality of sleeves;
   a tray having a plurality of rows, each row configured to hold at least one of: (i) one or more of the plurality of sleeves; and (ii) one or more of the plurality of carriers,
   wherein the tray is configured to at least one of: (i) unload the one or more sleeves or the one or more carriers from the tray; and (ii) load the one or more sleeves or the one or more carriers to the tray.

2. The automation system of claim 1, further comprising a loading area configured to hold the one or more carriers and provide the one or more carriers access to the track, and
   wherein the tray is further configured to at least one of: (i) unload the one or more sleeves or unload the one or more carriers from the tray to the loading area; and (ii) load the one or more sleeves or load the one or more carriers from the loading area to the tray.

3. The automation system of claim 2, further including a load-unload device configured to at least one of: (i) move the one or more sleeves or the one or more carriers between the tray and the track; and (ii) move the one or more sleeves or the one or more carriers between the tray and the loading area.

4. The automation system of claim 2, wherein the track comprises the loading area.

5. The automation system of claim 1, wherein the tray is further configured to at least one of: (i) unload the one or more sleeves or unload the one or more carriers through a bottom of the tray; and (ii) load the one or more sleeves or the one or more carriers through the bottom of the tray.

6. The automation system of claim 5, wherein the tray is further configured to at least one of: (i) unload each of the one or more sleeves or unload each of the one or more carriers substantially simultaneously from the tray; and (ii) load each of the one or more sleeves or load each of the one or more carriers substantially simultaneously to the tray.

7. The automation system of claim 1, wherein the tray is further configured to at least one of: (i) unload the one or more sleeves or unload the one or more carriers through an edge of the tray; and (ii) load the one or more sleeves or load the one or more carriers through the edge of the tray.

8. The automation system of claim 7, wherein the tray is further configured to at least one of: (i) unload a first row of the plurality of rows in parallel with a second row of the plurality of rows; and (ii) load the first row of the plurality of rows in parallel with the second row of the plurality of rows.

9. The automation system of claim 7, wherein the tray is configured to at least one of: (i) unload a sleeve or a carrier from a first row of the plurality of rows substantially simultaneous with a sleeve or a carrier from a second row of the plurality of rows; and (ii) load the sleeve or the carrier from the first row of the plurality of rows substantially simultaneous with the sleeve or the carrier from the second row of the plurality of rows.

10. The automation system of claim 1, wherein each of the plurality of carriers comprises an onboard processor that monitors one or more carrier parameters from a group of carrier parameters comprising a direction, a speed, a velocity, a distance from another carrier, and a payload.

* * * * *